US009776976B2

(12) United States Patent
Stock et al.

(10) Patent No.: US 9,776,976 B2
(45) Date of Patent: Oct. 3, 2017

(54) TRIAZOLONE COMPOUNDS AND USES THEREOF

(71) Applicant: Inception 2, Inc., San Diego, CA (US)

(72) Inventors: Nicholas Simon Stock, Encinitas, CA (US); Austin Chih-Yu Chen, San Marcos, CA (US); Yalda Mostofi Bravo, San Diego, CA (US); Jason Duarte Jacintho, San Diego, CA (US)

(73) Assignee: Inception 2, Inc., San Diego, CA (US)

( * ) Notice: Subject to any disclaimer, the term of this patent is extended or adjusted under 35 U.S.C. 154(b) by 0 days.

(21) Appl. No.: 14/916,860

(22) PCT Filed: Sep. 4, 2014

(86) PCT No.: PCT/US2014/054108
§ 371 (c)(1),
(2) Date: Mar. 4, 2016

(87) PCT Pub. No.: WO2015/035059
PCT Pub. Date: Mar. 12, 2015

(65) Prior Publication Data
US 2016/0194292 A1 Jul. 7, 2016

Related U.S. Application Data

(60) Provisional application No. 61/874,956, filed on Sep. 6, 2013.

(51) Int. Cl.
*C07D 249/12* (2006.01)
*C07D 401/04* (2006.01)
*C07D 401/10* (2006.01)

(52) U.S. Cl.
CPC ......... *C07D 249/12* (2013.01); *C07D 401/04* (2013.01); *C07D 401/10* (2013.01)

(58) Field of Classification Search
None
See application file for complete search history.

(56) References Cited

U.S. PATENT DOCUMENTS 4,487,773 A   12/1984  Temple, Jr. et al.
5,284,957 A    2/1994  Huff
(Continued)

FOREIGN PATENT DOCUMENTS

AT           455547      2/2010
AU        2003300031     5/2004
(Continued)

OTHER PUBLICATIONS

Abd Ei-Samii et al. 1995, Synthesis of some new 3-mercapto-5-substituted-1,2,4-triazine-s-triazoles for evaluation as antimicrobial agents. Journal of Chemical Technology and Biotechnology 63(2):135-140.
(Continued)

*Primary Examiner* — Karl J Puttlitz
(74) *Attorney, Agent, or Firm* — Knobbe, Martens, Olson & Bear, LLP

(57) ABSTRACT

The invention disclosed herein is directed to compounds of Formula (1a) and (1b) and pharmaceutically acceptable salts thereof, which are useful in the treatment of prostate, breast, colon, pancreatic, human chronic lymphocyticδ leukemia, melanoma and other cancers. The invention also comprises pharmaceutical compositions comprising a therapeutically effective amount of compound of Formula (1a) or (1b), or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to (Continued)

** P<0.01 vs vehicle
ns, non-significant 30 mg/kg P.O of Example 29 in B16F10 (IV) metastasis model methods of treating prostate, breast, colon, pancreatic, chronic lymphocytic leukemia, melanoma and other cancers comprising administration of a therapeutically effective amount of a compound which is a dual antagonist of PPARα and PPARδ. The compounds and pharmaceutical compositions of the invention are also useful in the treatment of viral infections, such as HCV infections and HIV infections. The invention disclosed herein is also directed to a methods of preventing the onset of and/or recurrence of acute and chronic myeloid leukemia, as well as other cancers, comprising administration of a therapeutically effective amount of a dual antagonist of PPARα and PPARδ.

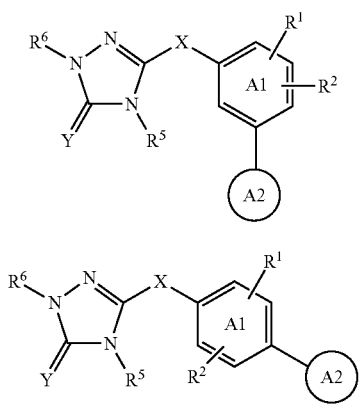

23 Claims, 1 Drawing Sheet

(56) References Cited

U.S. PATENT DOCUMENTS

| | | |
|---|---|---|
| 5,294,596 A | 3/1994 | Haas et al. |
| 5,550,244 A | 8/1996 | Kluth et al. |
| 5,629,311 A | 5/1997 | Hemmerle et al. |
| 5,856,495 A | 1/1999 | Weckbecker et al. |
| 7,816,522 B2 | 10/2010 | Clark |
| 7,816,822 B2 | 10/2010 | Nashiki |
| 7,915,267 B2 | 3/2011 | Nara et al. |
| 2002/0052510 A1 | 5/2002 | Hamilton et al. |
| 2004/0116491 A1 | 6/2004 | King et al. |
| 2005/0043181 A1 | 2/2005 | Feucht et al. |
| 2007/0032488 A1 | 2/2007 | Botyanszki et al. |
| 2009/0137603 A1 | 5/2009 | Nara et al. |
| 2009/0306397 A1 | 12/2009 | Bruns et al. |
| 2010/0022540 A1 | 1/2010 | Eggenweiler et al. |
| 2010/0331397 A1 | 12/2010 | Beigelman et al. |
| 2011/0195993 A1 | 8/2011 | Masson et al. |
| 2011/0319458 A1 | 12/2011 | Jin et al. |
| 2012/0208852 A1 | 8/2012 | Fuerstner et al. |
| 2015/0080412 A1 | 3/2015 | Stock et al. |
| 2015/0344446 A1 | 12/2015 | Stock et al. |

FOREIGN PATENT DOCUMENTS

| | | |
|---|---|---|
| BE | 894856 | 2/1983 |
| CA | 1263114 | 11/1989 |
| CN | 1629142 | 6/2005 |
| CN | 1993332 | 7/2007 |
| DE | 160447 | 8/1983 |
| DE | 3238590 | 4/1984 |
| DE | 19521162 | 12/1996 |
| DE | 19601189 | 7/1997 |
| EP | 0 067 508 | 12/1982 |
| EP | 0 060 697 | 12/1986 |
| EP | 0 273 310 | 7/1988 |
| EP | 0 422 469 | 4/1991 |
| EP | 0 513 766 | 11/1992 |
| EP | 0 540 318 | 5/1993 |
| EP | 0 665 227 | 8/1995 |
| EP | 1 834 953 | 9/2007 |
| EP | 2 330 098 | 6/2011 |
| FR | 2535168 | 5/1984 |
| GB | 2293169 | 3/1996 |
| GB | 2435827 | 9/1997 |
| GB | 2435828 | 9/1997 |
| GB | 2435829 | 9/1997 |
| IN | 183333 | 11/1999 |
| JP | 60-215675 | 10/1985 |
| JP | 2012-106996 | 6/2012 |
| KR | 2011088737 | 8/2011 |
| NL | 8204109 | 5/1984 |
| WO | WO 92/04346 | 3/1992 |
| WO | WO 93/21181 | 10/1993 |
| WO | WO 94/11357 | 5/1994 |
| WO | WO 95/25443 | 9/1995 |
| WO | WO 96/11196 | 4/1996 |
| WO | WO 96/13264 | 5/1996 |
| WO | WO 96/34851 | 11/1996 |
| WO | WO 96/37492 | 11/1996 |
| WO | WO 97/01553 | 1/1997 |
| WO | WO 97/01554 | 1/1997 |
| WO | WO 97/40017 | 10/1997 |
| WO | WO 98/04135 | 2/1998 |
| WO | WO 98/15277 | 4/1998 |
| WO | WO 98/18496 | 5/1998 |
| WO | WO 98/43962 | 10/1998 |
| WO | WO 99/03835 | 1/1999 |
| WO | WO 99/26945 | 6/1999 |
| WO | WO 99/62880 | 12/1999 |
| WO | WO 99/62888 | 12/1999 |
| WO | WO 00/09102 | 2/2000 |
| WO | WO 00/09103 | 2/2000 |
| WO | WO 00/09125 | 2/2000 |
| WO | WO 00/12489 | 3/2000 |
| WO | WO 00/71118 | 11/2000 |
| WO | WO 00/32588 | 2/2001 |
| WO | WO 01/46167 | 6/2001 |
| WO | WO 02/02555 | 1/2002 |
| WO | WO 02/20489 | 3/2002 |
| WO | WO 02/20501 | 3/2002 |
| WO | 0238553 | * 5/2002 |
| WO | WO 02/38553 | 5/2002 |
| WO | WO 01/90102 | 6/2002 |
| WO | WO 03/000682 | 1/2003 |
| WO | WO 03/051315 | 6/2003 |
| WO | WO 03/066050 | 8/2003 |
| WO | WO 03/084948 | 10/2003 |
| WO | WO 03/106448 | 12/2003 |
| WO | WO 2004/032840 | 4/2004 |
| WO | WO 2004/074257 | 9/2004 |
| WO | WO 2004/089306 | 10/2004 |
| WO | WO 2004/089380 | 10/2004 |
| WO | WO 2005/054179 | 6/2005 |
| WO | WO 2005/058848 | 6/2005 |
| WO | WO 2005/077178 | 8/2005 |
| WO | WO 2005/077345 | 8/2005 |
| WO | WO 2005/080379 | 9/2005 |
| WO | WO 2005/095362 | 10/2005 |
| WO | WO 2006/044732 | 4/2006 |
| WO | WO 2006/047195 | 5/2006 |
| WO | WO 2006/068199 | 6/2006 |
| WO | WO 2006/074984 | 7/2006 |
| WO | WO 2006/078698 | 7/2006 |
| WO | WO 2006/083645 | 8/2006 |
| WO | WO 2006/109056 | 10/2006 |
| WO | WO 2007/064797 | 6/2007 |
| WO | WO 2007/085349 | 8/2007 |
| WO | WO 2007/107758 | 9/2007 |
| WO | WO 2007/139955 | 12/2007 |
| WO | WO 2008/006499 | 1/2008 |
| WO | WO 2008/017594 | 2/2008 |

(56) References Cited

FOREIGN PATENT DOCUMENTS

| WO | WO 2008/103574 | 8/2008 |
|---|---|---|
| WO | WO 2008/119662 | 10/2008 |
| WO | WO 2008/127349 | 10/2008 |
| WO | WO 2008/128335 | 10/2008 |
| WO | WO 2009/014910 | 1/2009 |
| WO | WO 2009/017863 | 2/2009 |
| WO | WO 2009/019472 | 2/2009 |
| WO | WO 2009/023402 | 2/2009 |
| WO | WO 2009/052078 | 4/2009 |
| WO | WO 00/29386 | 5/2009 |
| WO | WO 2009/074782 | 6/2009 |
| WO | WO 2009/126863 | 10/2009 |
| WO | WO 2009/151529 | 12/2009 |
| WO | WO 2010/015212 | 2/2010 |
| WO | WO 2010/023946 | 3/2010 |
| WO | WO 2010/048207 | 4/2010 |
| WO | WO 2010/098600 | 9/2010 |
| WO | WO 2010/139966 | 12/2010 |
| WO | WO 2011/058478 | 5/2011 |
| WO | WO 2011/103546 | 8/2011 |
| WO | WO 2011/107530 | 9/2011 |
| WO | WO 2011/120926 | 10/2011 |
| WO | WO 2011/126903 | 10/2011 |
| WO | WO 2011/128316 | 10/2011 |
| WO | WO 2011/082400 | 11/2011 |
| WO | WO 2012/021455 | 2/2012 |
| WO | WO 2012/027482 | 3/2012 |
| WO | WO 2012/037299 | 3/2012 |
| WO | WO 2012/058531 | 5/2012 |
| WO | WO 2013/134562 | 9/2013 |
| WO | WO 2014/099503 | 6/2014 |

OTHER PUBLICATIONS

Ammazzalorso et al., 2011, Benzothiazole-based N-(phenylsulfonyl)amides as a novel family of PPARα antagonists, Bioorg. Med. Chem. Lett. 21:4869-4872.
Argentine et al., 2009, The Role of New Technologies in Defining a Manufacturing Process for PPARα Agonist LY518674, Organic Process Research & Development, 13(2):131-143.
Braden et al., 2007, A Convergent Kilogram-Scale Synthesis of the PPARα Agonist LY518674: Discovery of a Novel Acid-Mediated Triazolone Synthesis, Organic Process Research & Development, 11(3):431-440.
Bravo et al., 2014, Identification of the first potent, selective and bioavailable PPARα antagonist, Bioorganic & Medicinal Chemistry Letters, 24:2267-2272.
Deng et al., 2005, A novel and efficient synthesis of 2,5-substituted 1,2,4-triazol-3-ones. Tetrahedron Letters 46(46):7993-7996.
Etgen et al., 2003, PPAR ligands for metabolic disorders, Current Topics in Medicinal Chemistry, 3:1649-1661.
Girard, 1941, Tautomeric oxotriazoles and hydroxytriazoles. A new method for the preparation of hydroxy-1,2,4-triazoles, Compt rend. 212:547-549.
Goldin et al., 1974, Synthesis of triazolones and c-aminotriazoles by thermal condensation of carbamidoamidrazones, Chemistry of Heterocyclic Compounds 10(4):489-490.

Hanif et al., 2008, 5-(3-Methoxyphenethyl)-4-(2-methoxyphenyl)-4H-1,2,4-triazol-3-ol, Acta Crystallographica, Section E: Structure Reports Online, E64(11):o2180, sup-1-sup-9.
Hanif et al., 2009, 4-(3-Methoxyphenyl)-3-[2-(4-methoxyphenypethyl]-1H-1,2,4-triazol-5(4H)-one, Acta Crystallographica, Section E: Structure Reports Online, E65(2):o387, sup-1-sup-11.
Hanif et al., 2009, 4-(4-Methoxyphenyl)-3-[2-(2-methoxyphenyl)ethyl]-1H-1,2,4-triazol-5(4H)-one, Acta Crystallographica, Section E: Structure Reports Online, E65(2):0429, sup-1-sup-8.
International Search Report and Written Opinion dated Dec. 26, 2014 in PCT/US14/054108.
Kuecuekguezel et al., 2007, Synthesis of some novel heterocyclic compounds derived from diflunisal hydrazide as potential anti-infective and anti-inflammatory agents, European Journal of Medicinal Chemistry, 42:893-901.
Kuo et al,, 2007, The synthesis of three isotopomers of 2-methyl-2-(4-[3-[1-(4-methylbenzyl)-5-oxo-4,5-dihydro-1H-[1,2,4]triazol-3-yl]propyl]phenoxy)propionic acid, a potent and selective peroxisome proliferator-activated receptor alpha agonist, Journal of Labelled Compounds and Radiopharmaceuticals, 50(8):693-701.
Messmer et al., Dec. 8-11, 2012, 3879 Inhibition of fatty acid oxidation leads to apoptosis of resting and proliferating chronic lymphocytic leukemia cells in vitro, 54th ASH Annual Meeting and Exposition, Atlanta, GA, Oral and Poster Abstracts, 1 p.
Millar et al., 2009, Potent and selective PPAR-α agonist LY518674 upregulates both ApoA-I production and catabolism in human subjects with the metabolic syndrome, Arteriosclerosis, Thrombosis, and Vascular Biology, 29(1):140-146.
Moenes et al., Feb. 1996, Synthesis and antimicrobial activity of certain pyradazines, Alex. J. Pharm. Sci., 10(1)35-38.
Rao et al., 2010, Synthesis of substituted 2,4-dihydro[1,2,4]-triazol-3-ones, Indian Journal of Heterocyclic Chemistry 20(1):9-12.
Rashad et al., 2010, Synthesis of new quinoline derivatives as inhibitors of human tumor cells growth, Archiv der Pharmazie (Weinheim, Germany) 343(8):440-448.
Soliman et al., 2007, Heterocyclic synthesis with biologically active S-(6-aryl pyridazin 3-yl) thioglycollic acid hydrazides, Egypt. J. Chem. 50(4):443-453.
Tumosiene et al., 2007, Synthesis of azoles from 3,3'-(arylimino)bis[propanoyl hydrazides]. Chemistry of Heterocyclic Compounds (New York, NY, United States) 43(9):1148-1153.
Tumosiene et al., 2009, Synthesis of azole derivatives from 3-phenylaminopropanohydrazide and evaluation of their antimicrobial efficacy, Heterocycles, 78(1):59-70.
Tumosiene et al., 2009, Synthesis of azoles from 3,3'-[(4-alkoxyphenyl)imino]bis(propanoic acid hydrazides), Monatshefte fuer Chemie, 140(12):1523-1528.
Tutoveanu et al., 1973, New semi- and thiosemicarbazides and cyclization products, Revistade Chimie (Bucharest, Romania) 24(3):155-158.
Xu et al., 2003, Journal of Medicinal Chemistry 46:5121-5124.
Suchanek et al., 2002, Peroxisome proliferator-activated receptor α in the human breast cancer cell lines MCF-7 and MDA-MB-231, Molecular Carcinogenesis, 34:165-171.
Extended European Search Report dated Jan. 1, 2017 in patent application No. 14842357.7.

* cited by examiner

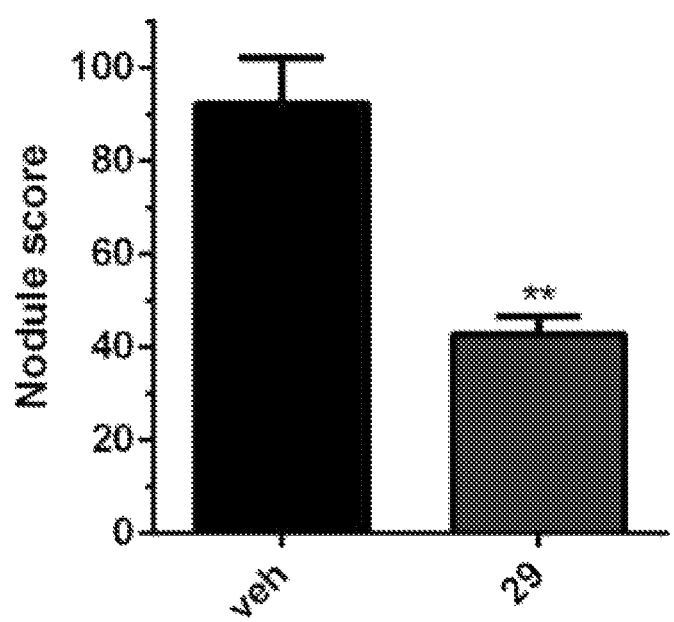
** P<0.01 vs vehicle
ns, non-significant
30 mg/kg P.O of Example 29 in B16F10 (IV) metastasis model

TRIAZOLONE COMPOUNDS AND USES THEREOF

RELATED APPLICATIONS

This application is the National Phase Entry of PCT/US2014/0541128, filed Sep. 4, 2014, which claims the benefit of U.S provisional patent application no. 61/874,956 entitled "TRIAZOLONE COMPOUNDS AND USES THEREOF" filed on Sep. 6, 2013, which is incorporated by reference in its entirety.

FIELD OF THE INVENTION

This invention is directed to novel triazolones, or pharmaceutically acceptable salts thereof. These compounds are dual antagonists of PPARα and PPARδ, and are useful in the treatment of prostate, breast, colon, pancreatic, human chronic lymphocytic leukemia, melanoma and other cancers. The invention disclosed herein is further directed to methods of treating prostate, breast, ovarian, liver, kidney, colon, pancreatic, human chronic lymphocytic leukemia, melanoma and other cancers comprising administration of a compound that is an antagonist of both PPARα and PPARδ. The compounds and pharmaceutical compositions of the invention are also useful in the treatment of viral infections, such as HCV infections and HIV infections.

BACKGROUND OF THE INVENTION

While tremendous strides have been made in the treatment of various cancers, in many cases, cancer treatment continues to be a matter of administering one or more anti-cancer agents that are marginally less chemotoxic to healthy cells than they are to the cancer in question. In recognition of this problem, there has been substantial research effort aimed at identifying, understanding and taking advantage of phenotypical behavior peculiar to certain cancer cells. It has long been observed that most cancer cell types generate energy for cellular processes through aerobic glycolysis rather than through oxidative phosphorylation as found in the normal cell. This process, which became known as the "Warburg effect", is highly energy inefficient and requires cancer cell mitochondria to resort to glucose fermentation to make up the energy deficit. Since perhaps the mid-1990's researchers have sought to identify methods of treating cancer that take advantage of the "Warburg effect" and associated aspects of cancer cell mitochondrial metabolism. See, for example, Wang, et. al., Small mitochondrial-targeting molecules as anti-cancer agents, Mol. Aspects Med. 2010 February; 31(1): 75-92.

Samudio, et. al., J. Clin. Invest. 120: 142-156 (2010), disclosed that in certain leukemia cell lines "mitochondrial uncoupling—the continuing reduction of oxygen without ATP synthesis—has recently been shown in leukemic cells to circumvent the ability of oxygen to inhibit glycolysis, and may promote the metabolic preference for glycolysis by shifting from pyruvate oxidation to fatty acid oxidation (FAO)." Samudio, et. al., also provided data indicating that inhibition of FAO could sensitize human leukemia cells to apoptosis, and further that inhibition of FAO may prove useful in the treatment of leukemia.

PPARα is known to be an important regulator of fatty acid oxidation. See Pyper, et. al., Nucl. Recept. Signal. 8:e002., e002 (2010). It has been reported that expression of the PPARα gene can be higher in human chronic lymphocytic leukemia (CLL) making this cancer type sensitive to therapies aimed at reducing FAO (Samudio et al., J. Clin. Invest. 120:142-156 (2010)). This effect may generalize to several cancer types. For example, ovarian cancer and breast cancer (Linher-Melville et al., 2011, BMC, 4; 11:56), thrive in an adipose rich environment and as a result can be negatively impacted by targeted therapies that reduce fatty acid metabolism (Nieman et al., 2011, Nat Med. 2011 Oct. 30; 17(11):1498-503). Still other cancers that rely on FAO include prostate cancer (Liu, Prostate Cancer Prostatic Dis., 2006; 9(3):230-4), colon cancer (Holla et al., 2011, JCB 286(34):30003-30009), pancreatic cancer (Khasawneh et al., 2009, PNAS, 106(9):3354-3359) and lung cancer (Zaugg et al., 2011, Genes and Development, 25:1041-1051).

GW6471 (Xu, et. al., Nature 415, 813-817 (2002)) and MK-866 (Kehrer, et. al., Biochem. J. 356, 899-906 (2001)) have been identified as antagonists of PPARα. Moreover, MK-866, whose primary activity is as an inhibitor of FLAP, has been disclosed to induce apoptosis in a human chronic lymphocytic leukemia cell line in a FLAP-independent manner; and has also been disclosed to induce apoptosis in prostate and glioblastoma cell lines.

Similar to PPARα, PPARδ is involved in lipid metabolism and may enable a shift from glucose to fatty acid utilization (Vamecq, et. al., PPAR Research, Vol. 2012, ID 304760). PPARδ upregulates many of the same genes as PPARα and may compensate in PPARα deficient conditions. It may, therefore, be necessary to block both receptors with a dual antagonist in order to fully inhibit fatty acid oxidation. It is our belief that in cancers that rely heavily on FAO, antagonism of PPARα and/or PPARδ by small molecules provides a panoply of anti-cancer treatment opportunities to: reduce or halt proliferation; decrease or reverse immunosupression; enhance apoptosis; and increase susceptibility to other anti-cancer agents. These cancers include prostate, breast, colon and pancreatic cancer, among others.

Chronic myeloid leukemia (CML) is model of hematopoietic stem cell (HSC) disease. In 2008, Ito et al, disclosed evidence linking the loss of promyelocytic leukemia (PML) gene expression with favorable outcomes in CML (Nature, 2008 Jun. 19; 453 (7198) 1072-1078). More recently Ito et al., disclosed that in the PML pathway, loss of PPARδ and accompanying inhibition of mitochondrial FAO induced loss of hematopoietic stem cell (HSC) maintenance (Nature Medicine 18, 1350-1358 (2012)). Moreover, Carracedo et al., disclosed that whereas PML expression allowed luminal filling in 3D basement membrane breast cancer, the effect was reversed by inhibition of FAO (J. Clin. Invest. 2012; 122(9):3088-3100). This and other evidence support our view that inhibition of fatty acid oxidation, via antagonism of PPAR's (including PPARα), will prove effective in inhibiting leukemia stem cell differential, and therefore, prove effective in preventing the onset of and/or recurrence of acute and chronic myeloid leukemia, as well as other cancers.

PPARα antagonists have also been shown to inhibit HCV replication and thereby prove useful in the treatment of HCV infection (Rakic, B. et. al., Chem. & Biol. 13, 23-30 (January 2006)). In some embodiments, PPAR modulators have been shown to inhibit viral transcription and replication and thereby prove useful in the treatment of viral diseases (Capeau et al., PPAR Research Volume 2009, Article ID 393408, 2 pages). In some embodiments, PPARα antagonists are useful in the treatment of HIV infection. PPARα antagonists have also been disclosed to be useful in the treatment of metabolic disorders (WO2012/027482A2).

Metabolic disorders include, but are not limited to diabetes, obesity, metabolic syndrome, impaired glucose tolerance, syndrome X, and cardiovascular disease.

SUMMARY OF THE INVENTION

The invention disclosed herein is directed to compounds of Formulae Ia and Ib

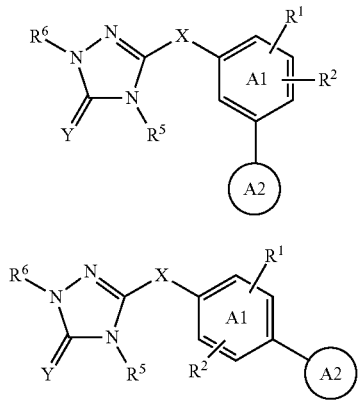

Ia

Ib and pharmaceutically acceptable salts thereof, which are useful in the treatment of prostate, breast, colon, pancreatic, human chronic lymphocytic leukemia, melanoma and other cancers. The invention also comprises pharmaceutical compositions comprising a therapeutically effective amount of compound of Formula Ia or Ib, or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, ovarian, liver, kidney, colon, pancreatic, human chronic lymphocytic leukemia, melanoma and other cancers comprising administration of a therapeutically effective amount of a compound that is an antagonist of both PPARα and PPARδ. The compounds and pharmaceutical compositions of the invention are also useful in the treatment of viral infections, such as HCV infections and HIV infections.

BRIEF DESCRIPTION OF THE DRAWINGS

FIG. 1 shows the ability of Example 29 to inhibit the metastasis of B16F10 melanoma cells to the lung.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

In one aspect the invention is directed to compounds of Formulae Ia and Ib

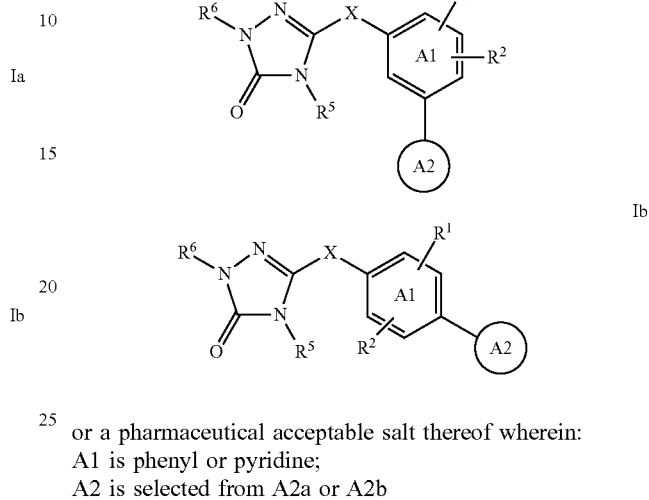

Ia

Ib or a pharmaceutical acceptable salt thereof wherein:
A1 is phenyl or pyridine;
A2 is selected from A2a or A2b

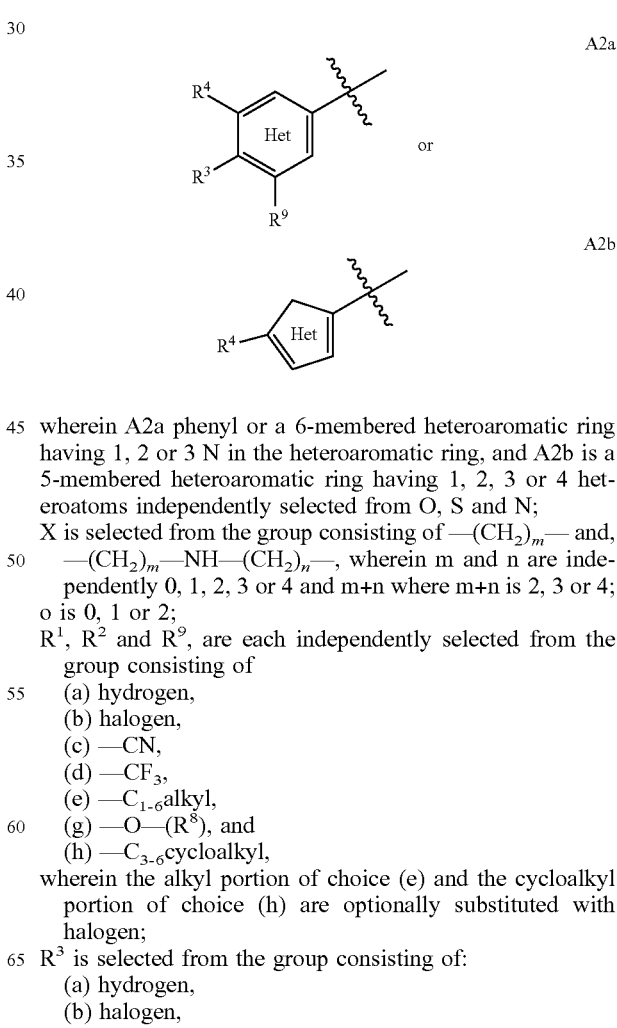

A2a or

A2b wherein A2a phenyl or a 6-membered heteroaromatic ring having 1, 2 or 3 N in the heteroaromatic ring, and A2b is a 5-membered heteroaromatic ring having 1, 2, 3 or 4 heteroatoms independently selected from O, S and N;
X is selected from the group consisting of —$(CH_2)_m$— and, —$(CH_2)_m$—NH—$(CH_2)_n$—, wherein m and n are independently 0, 1, 2, 3 or 4 and m+n where m+n is 2, 3 or 4;
o is 0, 1 or 2;
$R^1$, $R^2$ and $R^9$, are each independently selected from the group consisting of
(a) hydrogen,
(b) halogen,
(c) —CN,
(d) —$CF_3$,
(e) —$C_{1-6}$alkyl,
(g) —O—($R^8$), and
(h) —$C_{3-6}$cycloalkyl,
wherein the alkyl portion of choice (e) and the cycloalkyl portion of choice (h) are optionally substituted with halogen;
$R^3$ is selected from the group consisting of:
(a) hydrogen,
(b) halogen, (c) —CN,
(d) —CF₃,
(e) —C$_{1-6}$alkyl,
(f) —C$_{1-6}$alkyl-C(=O)OH,
(g) —O—(R⁸),
(h) —N(R⁷)(R⁸),
(i) —N(R⁷)S(=O)₂(R⁸),
(j) —C$_{3-6}$cycloalkyl, and
(k) heterocycle,
wherein the alkyl portion of choices (e) and (f), and the cycloalkyl portion of choice (j) are optionally substituted with halogen, oxo or hydroxyl, and
wherein the heterocycle of choice (k) are optionally mono- or di-substituted with substituents selected from the group consisting of halogen, nitro, —C$_{1-6}$alkyl, —C$_{1-6}$alkoxy, haloC$_{1-6}$alkyl, —C$_{3-6}$cycloalkyl, —C$_{3-6}$cycloalkoxy, —NH(C$_{1-6}$alkyl), —NH(C$_{3-6}$cycloalkyl), —N(C$_{1-6}$alkyl)₂, —N(C$_{3-6}$cycloalkyl)₂, —S(=O)$_o$C$_{1-6}$alkyl, —S(=O)$_o$C$_{3-6}$cycloalkyl, hydroxyl and —CN;

R⁴ is selected from the group consisting of:
(a) hydrogen,
(b) —N(R⁷)(R⁸),
(c) —N(R⁷)S(=O)₂R⁸,
(d) —N(R⁷)—C(=O)R⁸,
(e) —N(R⁷)C(=O)OR₈,
(f) —OC(=O)N(R⁷)(R⁸),
(g) —O—R⁸,
(h) —C$_{1-4}$alkyl-C(=O)NHS(=O)₂R⁷,
(i) —C$_{1-4}$alkyl-S(=O)₂NHC(=O)R⁷,
(j) —C$_{1-4}$alkyl-C(=O)—N(R⁷)(R⁸),
(k) —C$_{1-4}$alkyl-N(R⁷)C(=O)(R⁸),
(l) —C$_{1-4}$alkyl-N(R⁷)S(=O)₂(R⁸),
(m) —C$_{1-4}$alkyl-S(=O)₂N(R⁷)(R⁸),
(n) —C$_{1-4}$alkyl-N(R⁷)C(=O)O(R⁸),
(o) —C$_{1-4}$alkyl-O—C(=O)N(R⁷)(R⁸),
(p) —C$_{1-4}$alkyl-C(=O)(R⁷),
(q) —C$_{1-4}$alkyl-C(R⁷)(R⁸)OH,
(r) —C$_{1-4}$alkyl-O(R⁷),
(s) —C$_{1-6}$alkyl-C(=O)OH,
(t) —C$_{2-6}$alkenyl-C(=O)OH,
(u) —C$_{3-6}$cycloalkyl-C(=O)OH,
(v) —C$_{3-6}$cycloalkyl-C(=O)NHS(=O)₂R⁷,
(w) —C$_{3-6}$cycloalkyl-S(=O)₂NHC(=O)R⁷,
(x) —C$_{3-6}$cycloalkyl-C(=O)—N(R⁷)(R⁸),
(y) —C$_{3-6}$cycloalkyl-N(R⁷)C(=O)(R⁸),
(z) —C$_{3-6}$cycloalkyl-N(R⁷)S(=O)₂(R⁸),
(aa) —C$_{3-6}$cycloalkyl-S(=O)₂N(R⁷)(R⁸),
(bb) —C$_{3-6}$cycloalkyl-N(R⁷)C(=O)O(R⁸),
(cc) —C$_{3-6}$cycloalkyl-O—C(=O)N(R⁷)(R⁸),
(dd) —C$_{3-6}$cycloalkyl-C(=O)(R⁷),
(ee) —C$_{3-6}$cycloalkyl-C(R⁷)(R⁸)OH,
(ff) —C$_{3-6}$cycloalkyl-O(R⁷),
(gg) —C(=O)OH,
(hh) —C(=O)NR⁷S(=O)₂(R⁸),
(ii) —N(R⁷)S(=O)₂N(R⁸)₂, and
(jj) heterocycle,
wherein the alkyl portion of choices (h), (i), (j), (k), (l), (m), (n), (o), (p), (q), (r) and (s), the alkenyl portion of choice (t), and the cycloalkyl portion of choices (u), (v), (w), (x), (y), (z), (aa), (bb), (cc), (dd), (ee) and (ff), are optionally mono- or di-substituted with halogen, —C$_{1-6}$alkyl, —C$_{3-6}$cycloalkyl, —C$_{1-6}$alkoxy, —C$_{3-6}$cycloalkoxy, aryl, —C$_{1-6}$ alkylaryl, hydroxyl or oxo, and
wherein the heterocycle of choice (jj) is optionally mono- or di-substituted with substituents selected from the group consisting of halogen, nitro, —C$_{1-6}$alkyl, —C$_{1-6}$alkoxy, halo C$_{1-6}$alkyl, —C$_{3-6}$cycloalkyl, —C$_{3-6}$cycloalkoxy, —NH(C$_{1-6}$alkyl), —NH(C$_{3-6}$cycloalkyl), —N(C$_{1-6}$alkyl)₂, —N(C$_{3-6}$cycloalkyl)₂, —S(=O)$_o$C$_{1-6}$alkyl, —S(=O)$_o$C$_{3-6}$cycloalkyl, hydroxyl and CN,
with the proviso that at least one of R³ and R⁴ is other than hydrogen;

R⁵ is selected from the group consisting of:
(a) —C$_{1-6}$alkyl,
(b) —C$_{1-4}$alkyl(R⁷),
(c) -aryl,
(d) -heteroaryl,
(e) —C$_{3-6}$cycloalkyl,
(f) —C$_{3-6}$cycloalkyl(R⁷), and
(g) —C$_{2-6}$alkenyl,
wherein the alkyl portion of choice (a) and (b) is optionally substituted with halogen, the cycloalkyl portion of choice (e) and (f), is optionally substituted with halogen, the alkenyl of choice (g), is optionally substituted with halogen or C$_{1-4}$alkyl, and
wherein the aryl of choice (c) and the heteroaryl of choice (d), are optionally mono- or di-substituted with substituents selected from the group consisting of halogen, nitro, —C$_{1-6}$alkyl, —CF₃, —C$_{1-6}$alkoxy, halo C$_{1-6}$alkyl, aryl, heteroaryl, —C$_{3-6}$cycloalkyl, —C$_{3-6}$cycloalkoxy, and —CN;

R⁶ is selected from the group consisting of:
(a) aryl, and
(b) hetereoaryl,
wherein the aryl of choice (a), and the heteroaryl of choice (b), are optionally mono- or di-substituted with substituents selected from the group consisting of halogen, nitro, —CF₃, —OCF₃, —C$_{1-6}$alkyl, —C$_{1-6}$alkoxy, halo C$_{1-6}$alkyl, —NH(C$_{1-6}$alkyl), —N(C$_{1-6}$alkyl)₂, —N(C$_{3-6}$cycloalkyl)₂, —S(=O)$_o$C$_{1-6}$alkyl, —S(=O)$_o$C$_{3-6}$cycloalkyl, and —CN;

R⁷ and R⁸ are each independently selected from the group consisting of:
(a) hydrogen,
(b) —C$_{1-6}$alkyl,
(c) —C$_{3-6}$cycloalkyl,
(d) aryl,
(e) heteroaryl,
wherein the alkyl portion of choice (b), and the cycloalkyl portion of choice (c), are each optionally mono-, di- or tri-substituted with halogen, hydroxyl, —C$_{1-6}$alkyl, —C$_{1-6}$ alkoxy, —C$_{3-6}$cycloalkyl or —C$_{3-6}$cycloalkoxy, and wherein the aryl portion of choice (d), and the heteroaryl portion of choice (e), are each optionally mono- or di-substituted with substituents selected from the group consisting of halogen, nitro, —C$_{1-6}$alkyl, —C$_{1-6}$ alkoxy, haloC$_{1-6}$alkyl, —C$_{3-6}$cycloalkyl, —C$_{3-6}$cycloalkoxy, —NH(C$_{1-3}$ alkyl), —NH(C$_{3-6}$cycloalkyl), —N(C$_{1-3}$ alkyl)₂, —N(C$_{3-6}$cycloalkyl)₂, —S(=O)$_o$C$_{1-4}$alkyl, —S(=O)$_o$C$_{3-6}$cycloalkyl, —C(=O)C$_{1-4}$alkyl, aryl, heteroaryl, hydroxyl, CN, and —(C=O)OH.

In another aspect the invention is directed to compounds of Formulae Ia and Ib

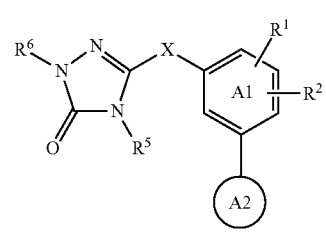

Ia

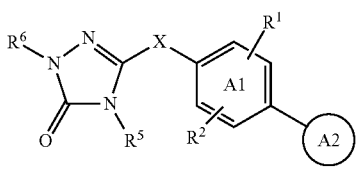

or a pharmaceutical acceptable salt thereof wherein:
A1 is phenyl;
A2 is selected from A2a or A2b

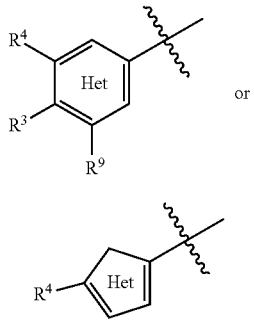

wherein A2a phenyl or a 6-membered heteroaromatic ring having 1, 2 or 3 N in the heteroaromatic ring, and
A2b is a 5-membered heteroaromatic ring having 1, 2, 3 or 4 heteroatoms independently selected from O, S and N;
X is selected from the group consisting of —$(CH_2)_m$— and, —$(CH_2)_m$—NH—$(CH_2)_n$—, wherein m and n are independently 0, 1, 2, 3 or 4 and m+n where m+n is 2, 3 or 4;
o is 0, 1 or 2;
$R^1$, $R^2$ and $R^9$, are each independently selected from the group consisting of
(a) hydrogen,
(b) halogen,
(c) —CN,
(d) —$CF_3$,
(e) —$C_{1-6}$alkyl,
(g) —O—($R^8$), and
(h) —$C_{3-6}$cycloalkyl,
wherein the alkyl portion of choice (e) and the cycloalkyl portion of choice (h) are optionally substituted with halogen;
$R^3$ is selected from the group consisting of:
(a) hydrogen,
(b) halogen,
(c) —CN,
(d) —$CF_3$,
(e) —$C_{1-6}$alkyl,
(f) —$C_{1-6}$alkyl-C(=O)OH,
(g) —O—($R^8$),
(h) —N($R^7$)($R^8$),
(i) —N($R^7$)S(=O)$_2$($R^8$),
(j) —$C_{3-6}$cycloalkyl, and
(k) heterocycle,
wherein the alkyl portion of choices (e) and (f), and the cycloalkyl portion of choice (j) are optionally substituted with halogen, oxo or hydroxyl, and
wherein the heterocycle of choice (k) are optionally mono- or di-substituted with substituents selected from the group consisting of halogen, nitro, —$C_{1-6}$alkyl, —$C_{1-6}$alkoxy, halo$C_{1-6}$alkyl, —$C_{3-6}$cycloalkyl, —$C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, hydroxyl and —CN;
$R^4$ is selected from the group consisting of:
(a) hydrogen,
(b) —N($R^7$)($R^8$),
(c) —N($R^7$)S(=O)$_2$$R^8$,
(d) —N($R^7$)—C(=O)$R^8$,
(e) —N($R^7$)C(=O)O$R_8$,
(f) —OC(=O)N($R^7$)($R^8$),
(g) —O—$R^8$,
(h) —$C_{1-4}$alkyl-C(=O)NHS(=O)$_2$$R^7$,
(i) —$C_{1-4}$alkyl-S(=O)$_2$NHC(=O)$R^7$,
(j) —$C_{1-4}$alkyl-C(=O)—N($R^7$)($R^8$),
(k) —$C_{1-4}$alkyl-N($R^7$)C(=O)($R^8$),
(l) —$C_{1-4}$alkyl-N($R^7$)S(=O)$_2$($R^8$),
(m) —$C_{1-4}$alkyl-S(=O)$_2$N($R^7$)($R^8$),
(n) —$C_{1-4}$alkyl-N($R^7$)C(=O)O($R^8$),
(o) —$C_{1-4}$alkyl-O—C(=O)N($R^7$)($R^8$),
(p) —$C_{1-4}$alkyl-C(=O)($R^7$),
(q) —$C_{1-4}$alkyl-C($R^7$)($R^8$)OH,
(r) —$C_{1-4}$alkyl-O($R^7$),
(s) —$C_{1-6}$alkyl-C(=O)OH,
(t) —$C_{2-6}$alkenyl-C(=O)OH,
(u) —$C_{3-6}$cycloalkyl-C(=O)OH,
(v) —$C_{3-6}$cycloalkyl-C(=O)NHS(=O)$_2$$R^7$,
(w) —$C_{3-6}$cycloalkyl-S(=O)$_2$NHC(=O)$R^7$,
(x) —$C_{3-6}$cycloalkyl-C(=O)—N($R^7$)($R^8$),
(y) —$C_{3-6}$cycloalkyl-N($R^7$)C(=O)($R^8$),
(z) —$C_{3-6}$cycloalkyl-N($R^7$)S(=O)$_2$($R^8$),
(aa) —$C_{3-6}$cycloalkyl-S(=O)$_2$N($R^7$)($R^8$),
(bb) —$C_{3-6}$cycloalkyl-N($R^7$)C(=O)O($R^8$),
(cc) —$C_{3-6}$cycloalkyl-O—C(=O)N($R^7$)($R^8$),
(dd) —$C_{3-6}$cycloalkyl-C(=O)($R^7$),
(ee) —$C_{3-6}$cycloalkyl-C($R^7$)($R^8$)OH,
(ff) —$C_{3-6}$cycloalkyl-O($R^7$),
(gg) —C(=O)OH,
(hh) —C(=O)N$R^7$S(=O)$_2$($R^8$),
(ii) —N($R^7$)S(=O)$_2$N($R^8$)$_2$, and
(jj) heterocycle,
wherein the alkyl portion of choices (h), (i), (j), (k), (l), (m), (n), (o), (p), (q), (r) and (s), the alkenyl portion of choice (t), and the cycloalkyl portion of choices (u), (v), (w), (x), (y), (z), (aa), (bb), (cc), (dd), (ee) and (ff), are optionally mono- or di-substituted with halogen, —$C_{1-6}$alkyl, —$C_{3-6}$cycloalkyl, —$C_{1-6}$alkoxy, —$C_{3-6}$cycloalkoxy, aryl, —$C_{1-6}$alkylaryl, hydroxyl or oxo, and
wherein the heterocycle of choice (jj) is optionally mono- or di-substituted with substituents selected from the group consisting of halogen, nitro, —$C_{1-6}$alkyl, —$C_{1-6}$alkoxy, halo $C_{1-6}$alkyl, —$C_{3-6}$cycloalkyl, —$C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, hydroxyl and —CN,
with the proviso that at least one of $R^3$ and $R^4$ is other than hydrogen;
$R^5$ is selected from the group consisting of:
(a) —$C_{1-6}$alkyl,
(b) —$C_{1-4}$alkyl($R^7$),
(c) -aryl,
(d) -heteroaryl,
(e) —$C_{3-6}$cycloalkyl,
(f) —$C_{3-6}$cycloalkyl($R^7$), and
(g) —$C_{2-6}$alkenyl,
wherein the alkyl portion of choice (a) and (b) is optionally substituted with halogen, the cycloalkyl portion of choice (e) and (f), is optionally substituted with halogen, the alkenyl of choice (g), is optionally substituted with halogen or $C_{1-4}$alkyl, and wherein the aryl of choice (c) and the heteroaryl of choice (d), are optionally mono- or di-substituted with substituents selected from the group consisting of halogen, nitro, —$C_{1-6}$alkyl, —$CF_3$, —$C_{1-6}$alkoxy, halo $C_{1-6}$alkyl, aryl, heteroaryl, —$C_{3-6}$cycloalkyl, —$C_{3-6}$cycloalkoxy, and —CN;

$R^6$ is selected from the group consisting of:
(a) aryl, and
(b) hetereoaryl, wherein the aryl of choice (a), and the heteroaryl of choice (b), are optionally mono- or di-substituted with substituents selected from the group consisting of halogen, nitro, —$CF_3$, —$OCF_3$, —$C_{1-6}$alkyl, —$C_{1-6}$alkoxy, halo $C_{1-6}$alkyl, —$NH(C_{1-6}$alkyl), —$N(C_{1-6}$alkyl)$_2$, —$N(C_{3-6}$cycloalkyl)$_2$, —$S(=O)_oC_{1-6}$alkyl, —$S(=O)_oC_{3-6}$cycloalkyl, and —CN;

$R^7$ and $R^8$ are each independently selected from the group consisting of
(a) hydrogen,
(b) —$C_{1-6}$alkyl,
(c) —$C_{3-6}$cycloalkyl,
(d) aryl, and
(e) heteroaryl, wherein the alkyl portion of choice (b), and the cycloalkyl portion of choice (c), are optionally mono-, di- or tri-substituted with halogen, hydroxyl, —$C_{1-6}$alkyl, —$C_{1-6}$alkoxy, —$C_{3-6}$cycloalkyl or —$C_{3-6}$cycloalkoxy, and wherein the aryl portion of choice (d), and the heteroaryl portion of choice (e), are optionally mono- or di-substituted with substituents selected from the group consisting of halogen, nitro, —$C_{1-6}$alkyl, —$C_{1-6}$alkoxy, halo $C_{1-6}$alkyl, —$C_{3-6}$cycloalkyl, —$C_{3-6}$cycloalkoxy, —$NH(C_{1-3}$ alkyl), —$NH(C_{3-6}$cycloalkyl), —$N(C_{1-3}$alkyl)$_2$, —$N(C_{3-6}$cycloalkyl)$_2$, —$S(=O)_oC_{1-4}$alkyl, —$S(=O)_oC_{3-6}$cycloalkyl, —$C(=O)C_{1-4}$alkyl, aryl, heteroaryl, hydroxyl, —CN, and —$(C=O)OH$.

Within this aspect there is a genus wherein:
A1 is phenyl;
A2 is selected from A2a or A2b

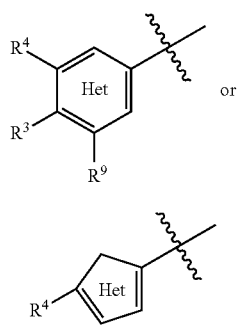

wherein A2a phenyl or a 6-membered heteroaromatic ring having 1, 2 or 3 N in the heteroaromatic ring, and A2b is a 5-membered heteroaromatic ring having 1, 2, 3 or 4 heteroatoms independently selected from O, S and N;

X is selected from the group consisting of —$(CH_2)_m$— and, —$(CH_2)_m$—NH—$(CH_2)_n$—, wherein m and n are independently 0, 1, 2, 3 or 4 and m+n where m+n is 2, 3 or 4;

$R^1$, $R^2$ and $R^9$, are each independently selected from the group consisting of
(a) hydrogen,
(b) halogen,
(c) —CN,
(d) —$CF_3$,
(e) —$C_{1-6}$alkyl,
(g) —O—($R^8$), and
(h) —$C_{3-6}$cycloalkyl, wherein the alkyl portion of choice (e) and the cycloalkyl portion of choice (h) are optionally substituted with halogen;

$R^3$ is selected from the group consisting of:
(a) hydrogen,
(b) —$CF_3$,
(c) —$C_{1-4}$alkyl,
(d) —O—($R^8$),
(e) —$N(R^7)S(=O)_2(R^8)$,
(f) —$C_{3-6}$cycloalkyl, and
(g) heterocycle, wherein the alkyl portion of choice (c), and the cycloalkyl portion of choice (f) are optionally substituted with halogen, oxo or hydroxyl, and wherein the heterocycle of choice (g) is optionally mono- or di-substituted with substituents selected from the group consisting of halogen, nitro, —$C_{1-6}$alkyl, —$C_{1-6}$alkoxy, halo $C_{1-6}$alkyl, —$C_{3-6}$cycloalkyl, —$C_{3-6}$cycloalkoxy, —$NH(C_{1-6}$alkyl), —$NH(C_{3-6}$cycloalkyl), —$N(C_{1-6}$alkyl)$_2$, —$N(C_{3-6}$cycloalkyl)$_2$, —$S(=O)_oC_{1-6}$alkyl, —$S(=O)_oC_{3-6}$cycloalkyl, hydroxyl and —CN;

$R^4$ is selected from the group consisting of:
(a) hydrogen,
(b) —$N(R^7)S(=O)_2R^8$,
(c) —O—$R^8$,
(d) —$C_{1-6}$alkyl-$C(=O)OH$,
(e) —$C_{3-6}$cycloalkyl-$C(=O)OH$,
(f) —$C(=O)OH$, and
(g) heterocycle, wherein the alkyl portion of choice (d) and the cycloalkyl portion of choice (e), are optionally mono- or di-substituted with halogen, —$C_{1-6}$alkyl, —$C_{3-6}$cycloalkyl, —$C_{1-6}$alkoxy, —$C_{3-6}$cycloalkoxy, aryl, —$C_{1-6}$alkylaryl, hydroxyl or oxo, and wherein the heterocycle of choice (g) is optionally mono- or di-substituted with substituents selected from the group consisting of halogen, nitro, —$C_{1-6}$alkyl, —$C_{1-6}$alkoxy, halo $C_{1-6}$alkyl, —$C_{3-6}$cycloalkyl, —$C_{3-6}$cycloalkoxy, —$NH(C_{1-6}$alkyl), —$NH(C_{3-6}$cycloalkyl), —$N(C_{1-6}$alkyl)$_2$, —$N(C_{3-6}$cycloalkyl)$_2$, —$S(=O)_oC_{1-6}$alkyl, —$S(=O)_oC_{3-6}$cycloalkyl, hydroxyl and CN, with the proviso that at least one of $R^3$ and $R^4$ is other than hydrogen;

$R^5$ is selected from the group consisting of:
(a) —$C_{1-6}$alkyl,
(b) —$C_{1-4}$alkyl($R^7$),
(c) -aryl,
(d) -heteroaryl,
(e) —$C_{3-6}$cycloalkyl,
(f) —$C_{3-6}$cycloalkyl($R^7$), and
(g) —$C_{2-6}$alkenyl, wherein the alkyl portion of choice (a) and (b) is optionally substituted with halogen, the cycloalkyl portion of choice (e) and (f), is optionally substituted with halogen, the alkenyl of choice (g), is optionally substituted with halogen or —$C_{1-4}$alkyl, and wherein the aryl of choice (c) and the heteroaryl of choice (d), are optionally mono- or di-substituted with substituents selected from the group consisting of halogen, nitro, —$C_{1-6}$alkyl, —$CF_3$, —$C_{1-6}$alkoxy, halo $C_{1-6}$alkyl, aryl, heteroaryl, —$C_{3-6}$cycloalkyl, —$C_{3-6}$cycloalkoxy, and —CN;

$R^6$ is selected from the group consisting of:
(a) aryl, and
(b) hetereoaryl,
wherein the aryl of choice (a), and the heteroaryl of choice (b), are optionally mono- or di-substituted with substituents selected from the group consisting of halogen, nitro, —$CF_3$, —$OCF_3$, —$C_{1-6}$alkyl, —$C_{1-6}$alkoxy, halo $C_{1-6}$alkyl, —NH($C_{1-6}$alkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, and —CN;

$R^7$ and $R^8$ are each independently selected from the group consisting of
(a) hydrogen,
(b) —$C_{1-6}$alkyl,
(c) —$C_{3-6}$cycloalkyl,
(d) aryl, and
(e) heteroaryl,
wherein the alkyl portion of choice (b), and the cycloalkyl portion of choice (c), are each optionally mono-, di- or tri-substituted with halogen, hydroxyl, —$C_{1-6}$alkyl, —$C_{1-6}$ alkoxy, —$C_{3-6}$cycloalkyl or —$C_{3-6}$cycloalkoxy, and wherein the aryl portion of choice (d), and the heteroaryl portion of choice (e), are each optionally mono- or di-substituted with substituents selected from the group consisting of halogen, nitro, —$C_{1-6}$alkyl, —$C_{1-6}$ alkoxy, halo$C_{1-6}$alkyl, —$C_{3-6}$cycloalkyl, —$C_{3-6}$cycloalkoxy, —NH($C_{1-3}$ alkyl), —NH($C_{3-6}$cycloalkyl), —N($C_{1-3}$ alkyl)$_2$, —N($C_{3-6}$cycloalkyl)$_2$, —S(=O)$_o$$C_{1-4}$alkyl, —S(=O)$_o$$C_{3-6}$cycloalkyl, —C(=O)$C_{1-4}$alkyl, aryl, heteroaryl, hydroxyl, —CN, and —(C=O)OH.

Within this aspect and this genus there is a sub-genus wherein:
X is selected from —$CH_2CH_2CH_2$ and —$CH_2$—NH—$CH_2$—.

Within this sub-genus there is a class wherein
X is —$CH_2CH_2CH_2$—.

Within this aspect and the genus which immediately follows it, there is a sub-genus wherein:
A2 is A2a.

Within this sub-genus there is a class wherein:
A2a is a substituted phenyl or substituted pyridine.

Within this aspect and the genus which immediately follows it, there is a sub-genus wherein:
$R^1$, $R^2$ and $R^9$ are each independently selected from the group consisting of
(a) hydrogen,
(b) —$CF_3$, and
(c) —$C_{1-6}$alkyl,
wherein the alkyl portion of choice (c) is optionally substituted with halogen.

Within this sub-genus there is a class wherein:
$R^1$, $R^2$ and $R^9$ are each independently selected from the group consisting of
(a) hydrogen, and
(b) methyl.

Within this aspect there is a genus wherein:
$R^3$ is selected from the group consisting of:
(a) hydrogen,
(b) —$CF_3$,
(c) —$C_{1-4}$alkyl,
(d) —O—($R^8$),
(e) —N($R^7$)S(=O)$_2$($R^8$),
(f) —$C_{3-6}$cycloalkyl, and
(g) heterocycle,
wherein the alkyl portion of choice (c), and the cycloalkyl portion of choice (f) are optionally substituted with halogen, oxo or hydroxyl, and
wherein the heterocycle of choice (g) are optionally mono- or di-substituted with substituents selected from the group consisting of halogen, nitro, —$C_{1-6}$alkyl, —$C_{1-6}$alkoxy, halo $C_{1-6}$alkyl, —$C_{3-6}$cycloalkyl, —$C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$ alkyl, —S(=O)$_o$$C_{3-6}$cycloalkyl, hydroxyl and —CN.

Within this aspect and and the genus immediately above there is a sub-genus wherein:
$R^3$ is selected from the group consisting of:
(a) hydrogen,
(b) —$CF_3$, and
(c) —O—($R^8$).

Within this aspect and the genus which immediately follows it there is a sub-genus wherein:
$R^4$ is selected from the group consisting of:
(a) hydrogen,
(b) —N($R^7$)S(=O)$_2$$R^8$,
(c) —$C_{1-6}$alkyl-C(=O)OH, and
(d) —C(=O)OH,
wherein the alkyl portion of choice (c) is optionally mono- or di-substituted with halogen, —$C_{1-6}$alkyl, —$C_{3-6}$cycloalkyl, —$C_{3-6}$cycloalkoxy, aryl, —$C_{1-6}$alkylaryl, hydroxyl or oxo.

Within this sub-genus there is a class wherein:
$R^4$ is selected from the group consisting of:
(a) hydrogen, and
(b) —$CH_2$—C(=O)OH.

Within this aspect and the genus which immediately follows it, there is a sub-genus wherein:
$R^5$ is selected from the group consisting of:
(a) —$C_{1-4}$alkyl,
(b) pyridinyl,
(c) phenyl, and
(d) —$C_{3-6}$cycloalkyl,
wherein the cycloalkyl portion of choice (d) is optionally substituted with halogen or methyl, and wherein the pyridinyl of choice (b) and the phenyl of choice (c) are optionally mono- or di-substituted with substituents selected from the group consisting of halogen, —$C_{1-6}$alkyl, —$CF_3$, —$C_{1-6}$alkoxy and halo $C_{1-6}$alkyl.

Within this aspect and the genus which immediately follows it there is a sub-genus wherein:
$R^6$ is selected from the group consisting of:
(a) aryl, and
(b) hetereoaryl,
wherein the aryl of choice (a), and the heteroaryl of choice (b), are optionally mono- or di-substituted with substituents selected from the group consisting of halogen, —$CF_3$, and —$C_{1-4}$alkyl.

Within this sub-genus there is a class wherein:
$R^6$ is selected from the group consisting of:
(a) phenyl, and
(b) pyridinyl,
wherein the phenyl of choice (a), and the pyridinyl of choice (b), are optionally mono-substituted with halogen, —$CF_3$, or —$C_{1-4}$alkyl.

Within this aspect and the genus which immediately followed it, there is a sub-genus wherein:
$R^7$ is selected from hydrogen and methyl; and
$R^8$ is selected from hydrogen, —$C_{1-4}$alkyl optionally substituted with halo, and phenyl optionally mono or di-substituted with substituents selected from the group consisting of halogen, —C$_{1-6}$alkyl, —C$_{1-6}$alkoxy, and haloC$_{1-6}$alkyl.

Within this aspect and the genus which immediately follows it, there is a sub-genus of Formula Ib,

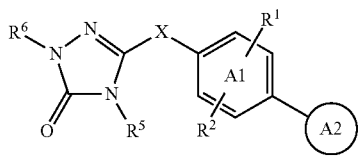

Ib or a pharmaceutically acceptable salt thereof

Within this aspect there is a genus of Formula Ib

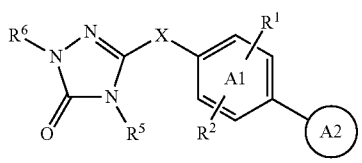

Ib or a pharmaceutically acceptable salt thereof, wherein:

X is selected from —CH$_2$CH$_2$CH$_2$—, and —CH$_2$—NH—CH$_2$—;

A1 is phenyl;

A2 is A2a;

R$^1$, R$^2$ and R$^9$ are each independently selected from the group consisting of
(a) hydrogen,
(b) —CF$_3$, and
(c) —C$_{1-6}$alkyl, wherein the alkyl portion of choice (c) is optionally substituted with halogen;

R$^3$ is selected from the group consisting of:
(a) hydrogen,
(b) —CF$_3$,
(c) —C$_{1-4}$alkyl,
(d) —O—(R$^8$),
(e) —N(R$^7$)S(=O)$_2$(R$^8$),
(f) —C$_{3-6}$cycloalkyl, and
(g) heterocycle, wherein the alkyl portion of choice (c), and the cycloalkyl portion of choice (f) are optionally substituted with halogen, oxo or hydroxyl, and wherein the heterocycle of choice (g) are optionally mono- or di-substituted with substituents selected from the group consisting of halogen, nitro, —C$_{1-6}$alkyl, —C$_{1-6}$alkoxy, halo C$_{1-6}$alkyl, —C$_{3-6}$cycloalkyl, —C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl, hydroxyl and CN;

R$^4$ is selected from the group consisting of:
(a) hydrogen,
(b) —N(R$^7$)S(=O)$_2$R$^8$,
(c) —C$_{1-6}$alkyl-C(=O)OH, and
(d) —C(=O)OH, wherein the alkyl portion of choice (c) is optionally mono- or di-substituted with halogen, —C$_{1-6}$alkyl, —C$_{3-6}$cycloalkyl, —C$_{1-6}$alkoxy, —C$_{3-6}$cycloalkoxy, aryl, —C$_{1-6}$alkylaryl, hydroxyl or oxo;

R$^5$ is selected from the group consisting of:
(a) —C$_{1-4}$alkyl,
(b) heteroaryl
(c) phenyl, and
(d) —C$_{3-6}$cycloalkyl, Wherein the cycloalkyl portion of choice (d) is optionally substituted with halogen or methyl, and wherein the heteroaryl of choice (b) and the heteroaryl of choice (c) is optionally mono- or di-substituted with substituents selected from the group consisting of halogen, —C$_{1-6}$alkyl, —CF$_3$, —C$_{1-6}$alkoxy and halo C$_{1-6}$alkyl;

R$^6$ is selected from the group consisting of:
(a) aryl, and
(b) hetereoaryl, wherein the aryl of choice (a), and the heteroaryl of choice (b), are optionally mono- or di-substituted with —CF$_3$;

R$^7$ is selected from hydrogen and methyl; and

R$^8$ is selected from hydrogen, C$_{1-4}$alkyl optionally substituted with halogen, and phenyl optionally mono or di-substituted with substituents selected from the group consisting of halogen, —C$_{1-6}$alkyl, —C$_{1-6}$alkoxy, and haloC$_{1-6}$alkyl.

Within this aspect there is a genus of Formula Ib

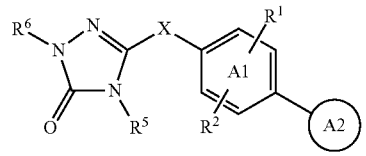

Ib or a pharmaceutically acceptable salt thereof, wherein:

X is selected from —CH$_2$CH$_2$CH$_2$—, and —CH$_2$—NH—CH$_2$—;

A1 is phenyl;

Ata is a substituted phenyl,

R$^1$, R$^2$ and R$^9$ are each independently selected from the group consisting of
(a) hydrogen, and
(b) methyl;

R$^3$ is selected from the group consisting of:
(a) hydrogen,
(b) —CF$_3$, and
(c) —O—(R$^8$);

R$^4$ is selected from the group consisting of:
(a) hydrogen, and
(b) —CH$_2$—C(=O)OH;

R$^5$ is selected from the group consisting of:
(a) —C$_{1-4}$alkyl,
(b) pyridinyl,
(c) phenyl, and
(d) —C$_{3-6}$ cycloalkyl, wherein the cycloalkyl portion of choice (d) is optionally substituted with halogen or methyl, and wherein the pyridinyl of choice (b) and the phenyl of choice (c) are optionally mono- or di-substituted with substituents selected from the group consisting of halogen, —C$_{1-6}$alkyl, —CF$_3$, —C$_{1-6}$alkoxy and halo C$_{1-6}$alkyl;

R$^6$ is selected from the group consisting of:
(a) phenyl, and
(b) pyridinyl, wherein the phenyl of choice (a), and the pyridinyl of choice (b), are optionally mono-substituted with —CF$_3$;

$R^7$ is selected from hydrogen and methyl; and $R^8$ is selected from hydrogen, C$_{1-4}$alkyl optionally substituted with halogen, and phenyl optionally mono or di-substituted with substituents selected from the group consisting of halogen, —C$_{1-6}$alkyl, —C$_{1-6}$alkoxy, and halo C$_{1-6}$alkyl.

Within this aspect and the genus which immediately follows it there is a sub-genus of Formula Ic

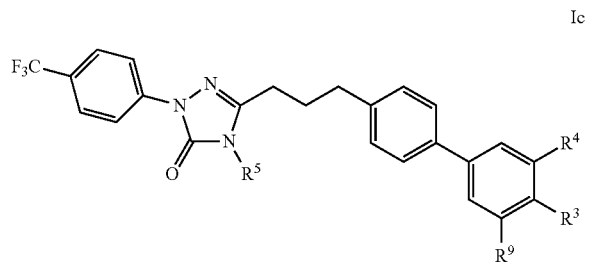

Ic or a pharmaceutically acceptable salt thereof

Within this sub-genus there is a class wherein $R^9$ is hydrogen.

Illustrating this aspect are Examples 1-41, or a pharmaceutically acceptable salt thereof The compounds of the invention are "dual antagonists" of both PPARα and PPARδ. (See the definition below.)

In one genus, the compound of the invention the ratio of the IC$_{50}$'s (PPARα :PPARδ or PPARδ :PPARα) is 10:1.

Within this genus, there is a sub-genus wherein the ratio is 5:1.

Many of the compounds are also selective for PPARα and/or PPARδ over PPARγ. (See the definition below)

In another aspect the invention is directed to a pharmaceutical composition comprising a compound of Formula I, or a pharmaceutically acceptable salt thereof, and a pharmaceutically acceptable carrier.

In another aspect the invention is directed to a method of treating a cancer which is negatively impacted by diminution in its metabolism of fatty acid oxidation via the administration of a therapeutically effective amount of a compound of Formula I, or a pharmaceutically acceptable salt thereof.

Within this aspect there is a genus wherein the cancer is selected from prostate, breast, ovarian, liver, kidney, colon, pancreatic, human chronic lymphocytic leukemia, and melanoma.

In another aspect the invention is directed to a method of treating cancer comprising the administration of a therapeutically effective amount of a compound of Formula I, or a pharmaceutically acceptable salt thereof.

In another aspect the invention is directed to a method of treating viral infection in a mammal comprising the administration of a therapeutically effective amount of a compound of Formula I, or a pharmaceutically acceptable salt thereof.

Within this aspect there is a genus wherein the viral infection is hepatitis C virus (HCV) infection or human immunodeficiency virus (HIV) infection.

In another aspect the invention is directed to a method of treating a metabolic disorder in a mammal comprising the administration of a therapeutically effective amount of a compound of Formula I, or a pharmaceutically acceptable salt thereof.

In another aspect the invention is directed to a method of preventing the onset of and/or recurrence of acute and chronic myeloid leukemia, as well as other cancers, through the administration of a therapeutically effective amount of a compound of Formula I, or a pharmaceutically acceptable salt thereof.

Definitions

The term "dual antagonist" or dual antagonists" is defined herein to a compound that has an IC$_{50}$ for the antagonism of both PPARα and PPARδ with activity of 1 μM or less as measured in the "Total Selectivity Assays", described below. For purposes of this specification, a compound is selective for PPARα (or PPARδ) over PPARγ, if the IC$_{50}$ for PPARα (or PPARδ) divided by the IC$_{50}$ for PPARγ is equal to or greater than 10.

"The term "patient" includes mammals such as mice, rats, cows, sheep, pigs, rabbits, goats, horses, monkeys, dogs, cats, and humans.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, C$_{1-6}$alkyl indicates that the group may have from 1 to 6 (inclusive) carbon atoms in it. In some embodiments, an alkyl is a C$_{1-6}$alkyl. Any atom can be optionally substituted, e.g., by one or more substitutents. Examples of alkyl groups include without limitation methyl, ethyl, n-propyl, isopropyl, n-butyl, sec-butyl and tert-butyl.

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substitutents. In some embodiments, a haloalkyl is a C$_{1-6}$haloalkyl. In some embodiments, a fluoroalkyl is a C$_{1-6}$fluoroalkyl.

As referred to herein, the term "alkoxy" refers to a group of formula —O-(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S-(alkyl). The terms "haloalkoxy" and "thioalkoxy" refer to —O-(haloalkyl) and —S-(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. In some embodiments, an alkenyl is a C$_{2-6}$alkenyl.

The term "heterocycle" or "heterocyclic" includes heterocycloalkyls and heteroaryls.

The term "heterocycloalkyl" as used herein except where noted, represents a stable 3-, 4-, 5-, 6- or 7-membered monocyclic- or stable 6-, 7-, 8-, 9-, 10-, 11-, or 12-membered fused bicyclic heterocyclic ring system which comprises at least one non-aromatic (i.e. saturated or partially unsaturated) ring which consists of carbon atoms and from one to four heteroatoms selected from the group consisting of N, O and S, wherein the nitrogen and sulfur heteroatoms may optionally be oxidized, and wherein the nitrogen heteroatom may optionally be quaternized. In some embodiments, a heterocycloalkyl is a $C_{2-10}$heterocycloalkyl. In other embodiments, a heterocycloalkyl is a $C_{2-6}$heterocycloalkyl. In some embodiments, a heterocycloalkyl is monocyclic. In some embodiments, a heterocycloalkyl is bicyclic. In the case of a "heterocycloalkyl" which is a bicyclic group, the second ring may also be a non-aromatic ring which consists of carbon atoms and from one to four heteroatoms selected from the group consisting of N, O and S, as defined above, or the second ring may be a benzene ring, or a "cycloalkyl", or a "cycloalkenyl", as defined immediately below. Examples of such heterocyclic groups include, but are not limited to, aziridine, azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, pyran, pyrazolidine, pyrazoline, pyrrolidine, pyrroline, tetrahydrofuran, tetrahydropyran, thiamorpholine, thiazoline, thiazolidine, thiomorpholine, and N-oxides thereof The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl). In some embodiments, a cycloalkyl is a $C_{3-10}$cycloalkyl. In other embodiments, a cycloalkyl is a $C_{3-6}$cycloalkyl. In some embodiments, a cycloalkyl is monocyclic. In some embodiments, a cycloalkyl is bicyclic.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclopentenyl, cyclohexenyl, cyclohexadienyl, or norbornenyl. In some embodiments, a cycloalkenyl is a $C_{4-10}$cycloalkenyl. In other embodiments, a cycloalkenyl is a $C_{4-6}$cycloalkenyl. In some embodiments, a cycloalkenyl is monocyclic. In some embodiments, a cycloalkenyl is bicyclic.

The term "cycloalkylene", as used herein, refers to a divalent monocyclic cycloalkyl group having the indicated number of ring atoms.

The term "heterocycloalkylene", as used herein, refers to a divalent monocyclic heterocyclyl group having the indicated number of ring atoms.

The term "aryl" as used herein, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, or biphenyl.

The term "heteroaryl", as used herein except where noted, represents a stable 5-, 6- or 7-membered monocyclic- or stable 9 or 10-membered fused bicyclic ring system which comprises at least one aromatic ring,—which consists of carbon atoms and from one to four heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, "heteroaryl" includes, for example, a stable 5-, 6- or 7-membered monocyclic aromatic ring consisting of carbon atoms and from one to four heteroatoms, as defined immediately above, fused to a benzene ring, or fused to a "heterocycloalkyl", a "cycloalkyl", or a "cycloalkenyl", as defined above. Examples of such heteroaryl groups include, but are not limited to, benzimidazole, benzisothiazole, benzisoxazole, benzofuran, isobenzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

Compound Forms and Salts

The compounds of this invention may contain one or more asymmetric centers and thus occur as racemates and racemic mixtures, enantiomerically enriched mixtures, single enantiomers, individual diastereomers and diastereomeric mixtures. The compounds of this invention include all cis, trans, syn, anti, entgegen (E), and zusammen (Z) isomers as well as the appropriate mixtures thereof. The compounds of this invention may also be represented in multiple tautomeric forms, in such instances, the invention expressly includes all tautomeric forms of the compounds described herein, even though only a single tautomeric form may be represented. All such isomeric forms of such compounds are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids.

When the compound of the present invention is acidic, salts may be prepared from pharmaceutically acceptable non-toxic bases, including inorganic and organic acids. Such salts that may be prepared include lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8] each of which is incorporated herein by reference in their entireties.

The compounds may be radiolabeled with radioactive isotopes, such as for example tritium, iodine-125 or carbon-14. All isotopic variations of the compounds of the invention, whether radioactive or not, are intended to be encompassed within the scope of the invention.

In some embodiments, hydrogen atoms of the compounds described herein may be replaced with deuterium atoms.

In some embodiments, compounds of Formula I are prepared as prodrugs. Prodrugs are generally drug precursors that, following administration to a subject and subsequent absorption, are converted to an active, or a more active species via some process, such as conversion by a metabolic pathway. Examples of prodrugs include $C_{1-6}$ alkyl esters of carboxylic acid groups, which, upon administration to a subject, are capable of providing active compounds.

Pharmaceutical Compositions

The term "pharmaceutically acceptable carrier" refers to a carrier or an adjuvant that may be administered to a patient, together with a compound of this invention, or a pharmaceutically acceptable salt thereof, and which does not destroy the pharmacological activity thereof and is nontoxic when administered in doses sufficient to deliver a therapeutic amount of the compound.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Uses

In one aspect the invention disclosed herein is directed to compounds of Formula I and pharmaceutically acceptable salts thereof, which are useful in the treatment of prostate, breast, ovarian, liver, kidney, colon, pancreatic, human chronic lymphocytic leukemia, melanoma and other cancers. In another aspect, the invention is directed to a method of preventing the onset of and/or recurrence of acute and chronic myeloid leukemia, as well as other cancers. The invention also includes pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, colon, pancreatic, human chronic lymphocytic leukemia, melanoma and other cancers comprising administration of a therapeutically effective amount of a selective PPARα antagonist. The methods include administering to the subject an effective amount of a compound of Formula (I) (and/or a compound of any of the other formulae described herein) or a salt (e.g., a pharmaceutically acceptable salt) thereof as defined anywhere herein to the patient. In another aspect, the use of a compound of Formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, alleviating, or slowing the progression of) or prevention (e.g., delaying the onset of or reducing the risk of developing) of one or more diseases, disorders, or conditions caused by, or associated with, prostate, breast, ovarian, liver, kidney, colon, pancreatic, human chronic lymphocytic leukemia, melanoma and other cancers.

In one aspect the invention is directed to a method of treating a cancer which is negatively impacted by diminution in its metabolism via fatty acid oxidation, comprising administration of a therapeutically effective amount of a compound of Formula I (and/or a compound of any of the other formulae described herein) or a salt (e.g., a pharmaceutically acceptable salt) there of. In another aspect, the invention is directed to a method of treating a cancer having a metabolism that is reliant on fatty acid oxidation, comprising administration of a therapeutically effective amount of a compound of Formula I (and/or a compound of any of the other formulae described herein), or a pharmaceutically acceptable salt thereof In another aspect the invention is directed to a method of treating viral infection, comprising administration of a therapeutically effective amount of compound of Formula I (and/or a compound of any of the other formulae described herein)" or a pharmaceutically acceptable salt thereof. Viral infections include hepatitis C virus (HCV) infection and human immunodeficiency virus (HIV) infection.

In another aspect the invention is directed to a method of treating a metabolic disorder, comprising administration of a therapeutically effective amount of compound of Formula I (and/or a compound of any of the other formulae described herein)" or a pharmaceutically acceptable salt thereof. Metabolic disorders include diabetes, obesity, metabolic syndrome, impaired glucose tolerance, syndrome X, and cardiovascular disease.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

In one aspect the compounds of the invention may be co-administered with one or more additional anti-cancer agents. The additional anti-cancer agents include, but are not limited to alkylating agents such as cyclophosphamide, chlorambucil, mecloreethamine, ifosfamide, or melphalan; antimetabolites such as methotrexate, cytarabine, fludarabine, 6-mercaptopurine, azathioprene, pyrimidines, or 5-fluorouracil; antimitotic agents such as vincristine, paclitaxel, vinorelbine or docetaxaxel; a topoisomerase inhibitors such as doxorubicin or irinotecan; platinum derivatives such as cisplatin, carboplatin or oxaliplatin; hormone therapeutics such as tamoxifen; aromatase inhibitors such as bicalutamide, anastrozole, exemestane or letrozole; signaling inhibitors such as imatinib, gefitinib or erlotinib; monoclonal antibodies such as rituximab, trastuzumab, gemtuzumab or ozogamicin; differentiating agents such as tretinoin or arsenic trioxide; antiangiogenic agents such as bevacizumab, sorafinib or sunitinib; biologic response modifiers such as interferon-alpha; topoisomerase inhibitors such as camptothecins (including irinotecan and topotecan), amsacrine, etoposide, etoposide phosphate, or teniposide; cytotoxic antibiotics such as actinomycin, anthracyclines including doxorubicin, daunorubicin, valrubicin, idarubicin, epirubicin, bleomycin, plicamycin or mitomycin; vinca alkaloids such as vincristine, vinblastine, viorelbine or vindesine; podophyllotoxins such as etoposide and teniposide; or mTOR inhibitors such as rapamycin, temsirolimus and everolimus.

Other anti-cancer agents for use in combination with the compounds include one or more of the following: abiraterone; adriamycin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; everolimus; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or r1L2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rapamycin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; temsirolimus; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In certain embodiments, the additional agents may be administered separately (e.g., sequentially; on different overlapping schedules), as part of a multiple dose regimen, from the compounds of this invention (e.g., one or more compounds of Formula (I) and/or a compound of any of the other formulae, including any subgenera or specific compounds thereof). In other embodiments, these agents may be part of a single dosage form, mixed together with the compounds of this invention in a single composition. In still another embodiment, these agents can be given as a separate dose that is administered at about the same time as that of one or more compounds of Formula (I) (and/or a compound of any of the other formulae, including any subgenera or specific compounds thereof) are administered (e.g., simultaneously with the administration of one or more compounds of Formula (I) (and/or a compound of any of the other formulae, including any subgenera or specific compounds thereof)). When the compositions of this invention include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase and then combined with emulsifying and/or suspending agents. If desired, certain sweetening and/or flavoring and/or coloring agents may be added.

Biological Function

The utility of the invention can be demonstrated by one or more of the following methods or other methods known in the art:
Human PPARα Reporter Assay The screening of test compounds for agonist or antagonist activities against human PPARα receptors was performed using a commercial kit, Human PPARα Reporter Assay System (Indigo Biosciences, Cat. #IB00111).

This nuclear receptor assay system utilizes proprietary non-human mammalian cells engineered to provide constitutive, high-level expression of Human PPARα. Because these cells incorporate a PPARα-responsive luciferase reporter gene, quantifying expressed luciferase activity provides a sensitive surrogate measure of PPARα activity in the treated cells. The primary application of this reporter assay system is in the screening of test samples to quantify any functional activity, either agonist or antagonist, that they may exert against human PPARα.

While this assay may be used to measure agonism, each of the Examples, vide infra, exhibits antagonism rather than agonism. Briefly, reporter cells are dispensed into wells of the assay plate and then immediately dosed with test compounds. Following an overnight incubation, the treatment media is discarded and Luciferase Detection Reagent (LDR) is added. The intensity of light emission from the ensuing luciferase reaction provides a sensitive measure that is directly proportional to the relative level of PPARα activation in the reporter cells.

| Example | PPARα Luciferase $IC_{50}$ (nM) | PPARδ Luciferase $IC_{50}$ (nM) | PPARγ (µM) | MS* (ESI) |
|---|---|---|---|---|
| 1 | 66 | 66 | 15.1 | 609 |
| 2 | 51 | 438 | 18.5 | 554 |
| 3 | 113 | 474 | 50.0 | 568 |
| 4 | 55 | 124 | 31.6 | 594 |
| 5 | 109 | 125 | 40.0 | 622 |

-continued

| Example | PPARα Luciferase IC$_{50}$ (nM) | PPARδ Luciferase IC$_{50}$ (nM) | PPARγ (μM) | MS* (ESI) |
|---|---|---|---|---|
| 6 | 135 | 154 | 18.1 | 622 |
| 7 | 324 | 220 | 19.4 | 622 |
| 8 | 29 | 505 | 27.1 | 624 |
| 9 | 250 | 312 | 39.8 | 634 |
| 10 | 192 | 198 | 28.1 | 644 |
| 11 | 42 | 124 | 24.8 | 620 |
| 12 | 424 | 667 | 54.1 | 621 |
| 13 | 182 | 1158 | >100 | 622 |
| 14 | 108 | 697 | 53.1 | 552 |
| 15 | 38794 | 8364 | >100 | 620 |
| 16 | 608 | 1622 | 23.5 | 634 |
| 17 | 43 | 485 | 30.7 | 580 |
| 18 | 23 | 18 | 45.4 | 602 |
| 19 | 31 | 32 | 22.3 | 637 |
| 20 | 150 | 363 | 32.9 | 582 |
| 21 | 30 | 67 | 55.2 | 620 |
| 22 | 88 | 61 | 44.5 | 638 |
| 23 | 216 | 30 | 14.9 | 638 |
| 24 | 21 | 138 | 18.4 | 658 |
| 25 | 343 | 100 | 29.0 | 630 |
| 26 | 420 | 83 | 14.9 | 632 |
| 27 | 28 | 236 | 28.9 | 611 |
| 28 | 165 | 789 | 32.9 | 659 |
| 29 | 113 | 25 | 15.0 | 620 |
| 30 | 386 | 96 | 27.6 | 620 |
| 31 | 199 | 742 | 56.9 | 567 |
| 32 | 56 | 131 | 63.2 | 606 |
| 33 | 138 | 746 | 32.3 | 655 |
| 34 | 678 | 3595 | 51.5 | 620 |
| 35 | 433 | 515 | 26.7 | 670 |
| 36 | 725 | 1244 | 79.0 | 620 |
| 37 | 17 | 34 | 27.7 | 670 |
| 38 | 569 | 47 | 48.0 | 603 |
| 39 | 111 | 34 | 20.0 | 634 |
| 40 | 80 | 40 | 37.4 | 616 |
| 41 | 126 | 61 | 31.0 | 603 |

*mass spectroscopic data

Target Selectivity Assays

To determine species selectivity, a Mouse PPARα Reporter Assay System was used (Indigo Biosciences, Cat. #M00111). Activity of test compounds to antagonize or agonize other isoforms of human PPAR, for example β/δ and γ, were assessed using the corresponding kits from Indigo Biosciences (Cat. #IB00121 and #IB00101, respectively). In addition to PPAR activity, compounds were also screened for activity against other nuclear hormone receptors including Estrogen Receptor β, Glucocorticoid Receptor and Thyroid Receptor β using commercially available kits (Indigo Biosciences, Cat. #IB00411, IB00201 and IB01101, respectively). Each assay system from Indigo Biosciences uses technology analogous to the human PPARα kit, with the variance being that the cells used for each assay were engineered to over-express the receptor of interest. In addition, the appropriate receptor agonist (included with each kit) was used at ~EC$_{80}$ for assays in which antagonist potency was being assessed.

| Target Selectivity - Counterscreen Assay Results | | | | | |
|---|---|---|---|---|---|
| Example | PPAR alpha IC$_{50}$ (nM) | PPAR beta/delta IC$_{50}$ (nM) | PPAR gamma IC$_{50}$ (μM) | Thyroid Receptor β IC$_{50}$ (μM) | Glucocorticoid Receptor IC$_{50}$ (μM) | Estrogen Receptor β IC$_{50}$ (μM) |
| 29 | 113 | 25 | 15000 | 29.8 | 25.1 | 15.5 |

Measuring Fatty Acid Oxidation Using $^3$H Palmitate
le;.3qFatty acid oxidation is measured using $^3$H palmitate metabolism into $^3$H$_2$O as described previously (Nieman et al., 2011). Briefly, cells (e.g. HepG2, PC3 and CLL) are plated in growth media and allowed to adhere overnight. Cells are then treated with compound or 40 μM etomoxir (an inhibitor of fatty acid oxidation) as control. After treatment, cells are washed with DPBS followed by incubation in assay buffer (growth media, $^3$H palmitate and compound). After incubation, media is collected and proteins precipitated with 5% trichloroacetic acid. The precipitate is pelleted by centrifugation and the supernatant collected. Any remaining $^3$H palmitate in the supernatant is then removed by purification over a Dowex anion exchange column. $^3$H$_2$O is then measured by scintillation counting.

Measurement of Cell Viability

Purified CLL cells were cultured at 2×10$^5$ cells/200 μL of RPMI1640 supplemented with 10% FCS in 96-well plates under various treatment conditions. Determination of CLL cell viability was based on the analysis of mitochondrial transmembrane potential (ΔΨm) using 3,3'-dihexyloxacarbocyanine iodide (DiOC6) (Invitrogen) and cell membrane permeability to propidium iodide (PI) (Sigma). For viability assays, 100 μL of the cell culture was collected at the indicated time points and transferred to polypropylene tubes containing 100 μL of 40 μM DiOC6 and 10 μg/mL PI in culture media. The cells were then incubated at 37° C. for 15 min and analyzed within 30 min by flow cytometry using an Accuri C6 flow cytometer. The percentage of viable cells was determined by gating on PI negative and DiOC6 bright cells.

In Vivo Cancer Model: B16F10 Model of Pulmonary Metastasis

B16F10 cells were cultured in standard growth media, harvested when approximately 50% confluent and injected into C57BL/6 mice via the tail vein (50,000 cells per mouse in 200 μL). Mice were then treated daily with test compound. On day 21, mice were euthanized. Lungs were harvested and placed into Fekete's solution overnight to facilitate visualization of the tumors. Black nodules were enumerated.

FIG. 1 shows inhibition of metastasis of B16F10 melanoma cells to the lung following intraperitoneal doses of example 29 at 0.3, 3 and 30 mg/kg. Example 29 inhibited metastasis of B16F10 melanoma cells to the lung in a dose dependent manner. Statistics were performed by ANOVA with Dunnett's Multiple Comparison Test post-hoc to determine statistical differences from vehicle treatment group (* denotes P<0.05 while *** denotes P<0.001).

SYNTHESIS

The starting materials used for the synthesis are either synthesized or obtained from commercial sources, such as, but not limited to, Sigma-Aldrich, Fluka, Acros Organics, Alfa Aesar, VWR Scientific, and the like. General methods for the preparation of compounds can be modified by the use of appropriate reagents and conditions for the introduction of the various moieties found in the structures as provided herein.

In some embodiments, compounds described herein are prepared as outlined in the following general synthetic scheme. Substituents R, R$^3$, R$^5$ and Het as used in the schemes are provided for illustrative purposes and are not intended to be limited to any particular choices of the definitions provided in the claims.

General Synthetic Scheme for Exemplary Compounds

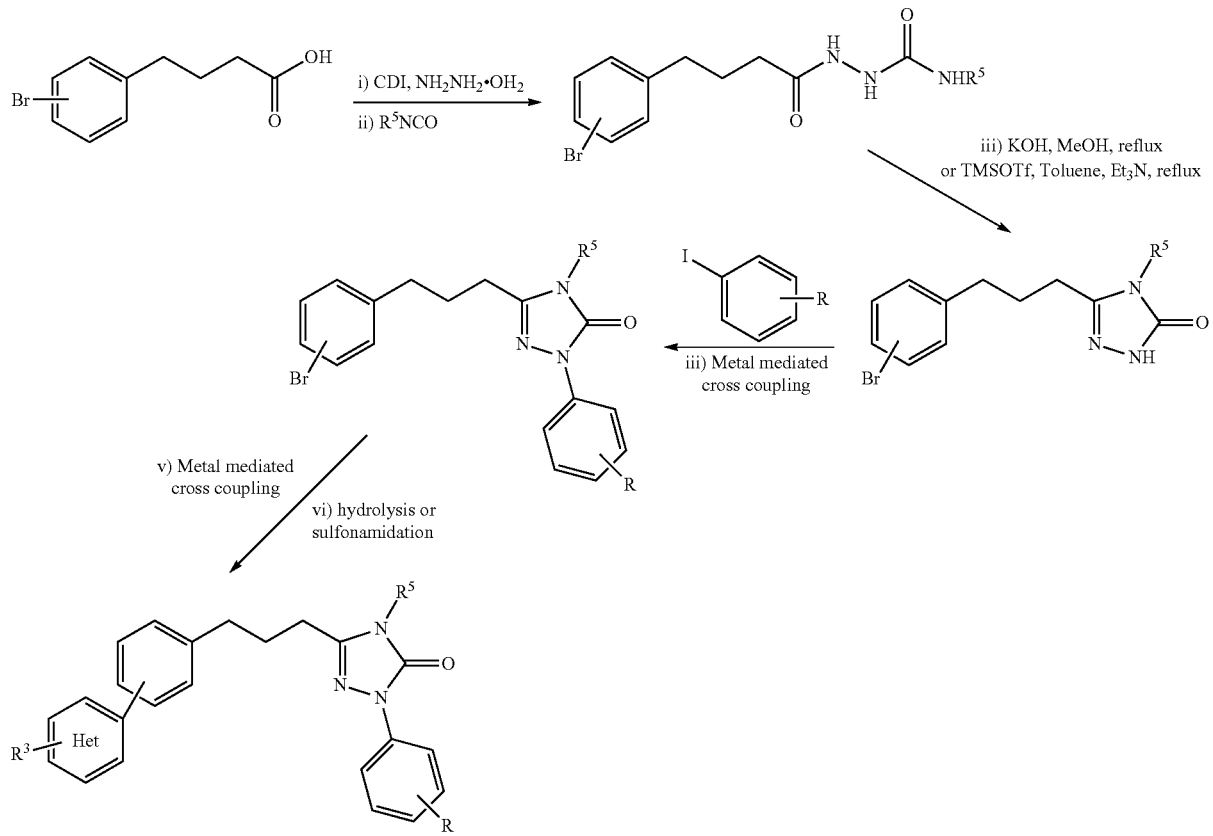

Representative Synthesis of Isocyanates

1-Isocyanato-4-methylcyclohexane: To a toluene (5 mL) solution of 4-methylcyclohexanecarboxylic acid (200 mg, 1.4 mmol, 1 eq.) and diphenylphosphoryl azide (0.33 mL, 1.5 mmol 1.1 eq.) was added dropwise neat triethylamine (0.23 mL, 1.7 mmol, 1.2 eq.). The resulting mixture was first allowed to stir at RT for 20 min, and then it was heated at reflux for 2 h to faciliate the rearrangement. After the reaction mixture was allowed to cool to RT, the volatiles were then removed in vacuo to furnish the title compound as a pale yellow oil. This was used as is without further purification.

1-Isocyanato-3-methylcyclohexane: Prepared as above but using instead 3-methylcyclohexanecarboxylic acid as the starting material.

1-Isocyanato-2-methylcyclohexane: Prepared as above but using instead 2-methylcyclohexanecarboxylic acid as the starting material.

4-(4-Bromophenyl)butanehydrazide

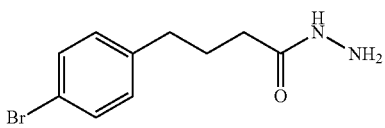 [SMILES: NNC(=O)CCCc1ccc(Br)cc1]

To a solution of 4-(4-bromophenyl)butanoic acid (10.2 g, 41.9 mmol) in THF (175 mL) was added carbonyldiimidazole (7.47 g, 46.1 mmol) and stirred at room temperature for 2 hr. Hydrazine hydrate (8.5 mL; ~4 eq) was added in one portion and stirring maintained for a period of 1 hr. The solvent was evaporated, the residue partitioned between EtOAc and water, extracted with EtOAc, dried (MgSO$_4$), filtered and evaporated to afford the title compound which is used without further purification.

Methyl 2-(5-bromo-2-hydroxyphenyl)acetate

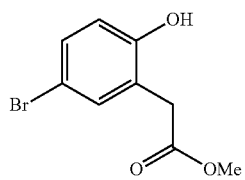 [SMILES: COC(=O)Cc1cc(Br)ccc1O]

To a solution of 2-(2-hydroxyphenyl)acetic acid (15.6 g, 103 mmol) in MeOH (350 mL) was added tetrabutylammonium tribromide (50 g, 103 mmol) in small portions over a 10 minute period. After stirring at ambient temperature for 24 hrs, the solvent was evaporated and the residue taken up in EtOAc and 1N aq. HCl. The aqueous wash was separated and back-extracted with EtOAc. The combined organic phases were then dried (MgSO$_4$), filtered and the filtrate concentrated in vacuo. The resulting residue was purified on silica gel eluting with a gradient of 30% EtOAc in hexanes to afford the title compound as a colorless solid.

Methyl 2-(5-bromo-2-ethoxyphenyl)acetate
1p;-2p

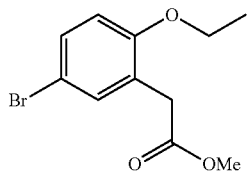

To a solution of methyl 2-(5-bromo-2-hydroxyphenyl) acetate (1.0 g, 4.1 mmol) in DMF (8 mL) was added cesium carbonate (2.66 g, 8.2 mmol) and iodoethane (392 µL, 4.9 mmol). After 2 hrs of stirring at rt, the reaction mixture was partitioned between EtOAc and water. The organic phase was then separated, washed with water, dried (MgSO$_4$), filtered and the filtrate concentrated in vacuo. The resulting residue was purified on silica gel eluting with a gradient of 0 to 10% EtOAc in hexanes to afford the title compound as a colorless oil.

Methyl 2-(2-ethoxy-5-(4,4,5,5-tetramethyl-1,3,2-dioxaborolan-2-yl)phenyl)acetate

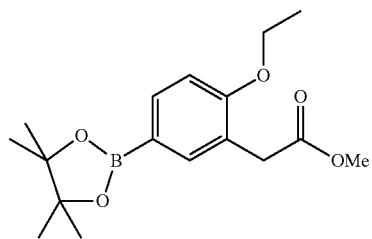 [SMILES: CCOc1ccc(B2OC(C)(C)C(C)(C)O2)cc1CC(=O)OC]

To a solution of methyl 2-(5-bromo-2-ethoxyphenyl)acetate (1.42 g, 5.2 mmol) in p-dioxane (35 mL) was added potassium acetate (1.53 g, 15.6 mmol), bis(pinacolato)diboron (1.6 g, 6.3 mmol) and Pd(dppf)Cl$_2$ (100 mg). The solution as degassed via sub-surface purging with dry nitrogen gas for 10 minutes, then heated at 85° C. under a nitrogen atmosphere for 12 hrs. After complete reaction, the suspension was allowed to cool, evaporated, the residue partitioned between EtOAc and water and the organic phase separated, dried (MgSO$_4$), filtered and evaporated in vacuo. The residue was purified on silica gel eluting with a gradient of 0 to 20% EtOAc in hexanes to afford the title compound as a colorless oil which solidified upon standing.

Methyl 2-(2-methoxy-5-(4,4,5,5-tetramethyl-1,3,2-dioxaborolan-2-yl)phenyl)acetate

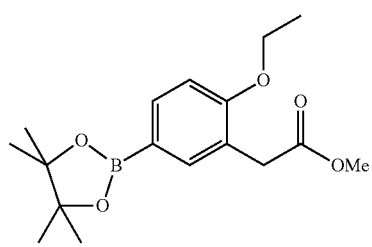 [SMILES: CCOc1ccc(B2OC(C)(C)C(C)(C)O2)cc1CC(=O)OC]

Prepared in an analogous fashion to the aforementioned ethyl derivative with methyl 2-(5-bromo-2-methoxyphenyl) acetate as the aryl bromide.

Methyl 2-(2-propoxy-5-(4,4,5,5-tetramethyl-1,3,2-dioxaborolan-2-yl)phenyl)acetate

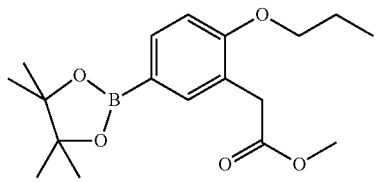 [SMILES: CCCOc1ccc(B2OC(C)(C)C(C)(C)O2)cc1CC(=O)OC]

Prepared in an analogous fashion to the aforementioned ethyl derivative with methyl 2-(5-bromo-2-propoxyphenyl) acetate as the aryl bromide.

Ethyl 5-bromo-2-ethoxybenzoate

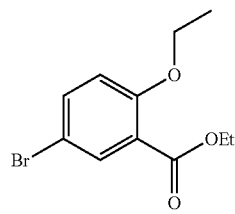

To a solution of ethyl 5-bromo-2-hydroxybenzoate (2.0 g, 8.66 mmol) in DMF (15 mL) was added cesium carbonate (5.64 g, 17.3 mmol) and iodoethane (762 µL, 9.63 mmol). After 2 hrs of stirring at rt, the reaction mixture was partitioned between EtOAc and water. The organic phase was then separated, washed with water, dried (MgSO$_4$), filtered and the filtrate concentrated in vacuo. The resulting residue was purified on silica gel eluting with a gradient of 0 to 20% EtOAc in hexanes to afford the title compound as a colorless oil.

4-(4-bromo-3-methylphenyl)butanehydrazide

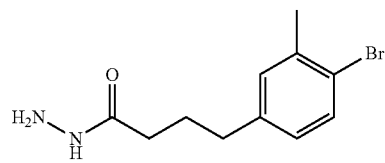

Step 1: To a solution of 4-bromo-3-methyl benzaldehyde (5.0 g, 24.6 mmol) in DMF (18 mL) was added sodium cyanide (241 mg, 4.9 mmol) in one rapid portion and the resulting dark red suspension was heated at 45° C. for 25 minutes. Acrylonitrile (1.53 mL, 4 mmol) was added dropwise as a DMF solution (3 mL) to the now dark brown reaction suspension over a period of 20 min. The final reaction mixture was allowed to heat at 45° C. for 3 hrs. The crude reaction mixture was then cooled to RT, carefully quenched with glacial acetic acid and water, and extracted with EtOAc. The combined organic extracts were washed further with water and brine, dried (MgSO$_4$), filtered and the filtrate concentrated in vacuo to afford a dark red, viscous oil. Further purification by column chromatography (SiO$_2$, gradient elution, Hex→30% EtOAc in hexanes) furnished 4-(4-bromo-3-methylphenyl)-4-oxobutanenitrile (3.7 g, 60% yield).

Step 2: To a solution of the previously isolated nitrile (3.4 g, 13.5 mmol) in ethylene glycol (23 mL) was added water (0.6 mL), hydrazine monohydrate (1.6 mL) and potassium hydroxide (3.7 g). The mixture was heated in a sealed vial at 195° C. for 3 hrs, allowed to cool, diluted with water and acidified with 2N HCl. The mixture was extracted with EtOAc, the organic phase separated, dried (MgSO$_4$), filtered and evaporated. The residue was purified by column chromatography on silica gel (0 to 30% acetone in hexanes) to afford 4-(4-bromo-3-methylphenyl)butanoic acid (2.1 g, 60% yield).

Step 3: To a solution of the previously isolated carboxylic acid (1.70 g, 6.6 mmol) in THF (20 mL) cooled to 0° C. was added carbonyl diimidazole (1.29 g, 7.9 mmol) and the solution stirred at ambient temperature for 48 hrs. The solution was cooled to 0° C. and hydrazine monohydrate (1.28 mL, 26.4 mmol) added and the mixture allowed to stir at room temperature for 4 hrs. The mixture was then evaporated in vacuo, the residue diluted in EtOAc and the organic phase washed sequentially with water, 1N NaOH (aq.) and brine, the organic phase separated, dried (Na$_2$SO$_4$), filtered and evaporated to afford a yellow solid. Recrystallization from EtOH afforded the title compound as a white solid (1.14 g, 64% yield).

Example 1

2-(4'43-(4-cyclohexyl-5-oxo-1-(4-(trifluoromethyl) phenyl)-4,5-dihydro-1H-1,2,4-triazol-3-yl)propyl)-4-ethoxy-[1,1'-biphenyl-]-3-yl)acetic acid

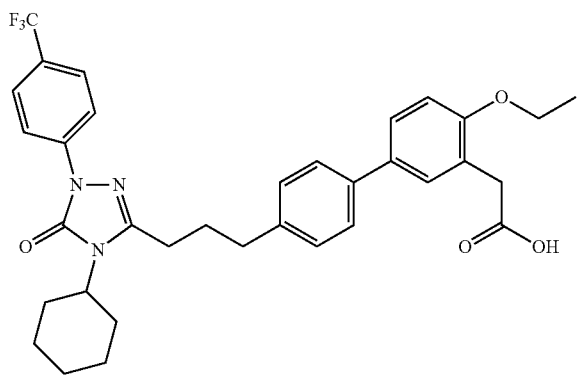 [SMILES: CCOc1ccc(-c2ccc(CCCc3nn(-c4ccc(C(F)(F)F)cc4)c(=O)n3C3CCCCC3)cc2)cc1CC(=O)O]

Step 1: To a DCM (20 mL) solution of 4-(4-bromophenyl) butanehydrazide (1.0 g, 3.9 mmol, 1 eq.) was added cyclohexyl isocyanate (0.82 mL, 5.9 mmol, 1.5 eq.) dropwise over a period of 5 min. The resulting solution was allowed to stir at RT for 13 h, becoming a white suspension. To this mixture was then added heptanes and the desired product was isolated as a white solid via vacuum filtration. This was used in the next step with no further purification.

Step 2: To a toluene (30 mL) solution of 2-(4-(4-bromophenyl)butanoyl)-N-cyclohexylhydrazinecarboxamide (1.49 g, 3.9 mmol, 1 eq.) from the previous step was added sequentially triethylamine (2.7 mL, 20 mmol, 5 eq.) and trimethylsilyl trifluoromethanesulfonate (2.1 mL, 12 mmol, 3 eq.). The resulting mixture was then heated at reflux for 20 h. After cooling to RT, the reaction was quenched with the addition of aq. NaHCO$_3$ and extracted with ether. The combined organic extracts were washed further with water and brine, dried over Na$_2$SO$_4$, filtered and the filtrate concentrated in vacuo to afford the crude product as viscous red oil. Purification by way of column chromatography (SiO$_2$, gradient elution, 1:1 (v/v) Hex: EtOAc→EtOAc) afforded the desired product as a colorless oil that solidified upon standing (710 mg, 50% yield).

Step 3: To a DMSO (10 mL) solution of 3-(3-(4-bromophenyl)propyl)-4-cyclohexyl-1H-1,2,4-triazol-5(4H)-one (0.71 g, 2.0 mmol, 1 eq.) from the previous step was added copper(I) iodide (37 mg, 0.2 mmol, 0.1 eq.), L-proline (45 mg, 0.39 mmol, 0.2 eq.), potassium carbonate (670 mg, 4.9 mmol, 2.5 eq.) and 4-iodobenzotrifluoride (0.43 mL, 2.9 mmol, 1.5 eq.). The resulting aqua blue solution was de-oxygenated via sub-surface purging with nitrogen for 15 min. The reaction vessel was then sealed and heated at 95° C. for 16 h. After cooling to RT, the reaction suspension was diluted with ether and washed sequentially with 10% aq. HCl, 1 N aq. NaOH, water and brine. The organic extract was then dried over Na$_2$SO$_4$, filtered and the filtrate concentrated in vacuo. Purification of the crude product thus obtained by way of column chromatography (SiO$_2$, gradient elution, 1:1 (v/v) Hex: EtOAc→EtOAc) afforded the desired product as a pale yellow oil (960 mg, 92% yield).

Step 4: To a DME (10 mL) solution of 3-(3-(4-bromophenyl)propyl)-4-cyclohexyl-1-(4-(trifluoromethyl)phenyl)-1H-1,2,4-triazol-5(4H)-one (0.96 g, 1.9 mmol, 1 eq.) from the previous step was added methyl 2-(2-ethoxy-5-(4,4,5,5-tetramethyl-1,3,2-dioxaborolan-2-yl)phenyl)acetate (0.79 g, 2.5 mmol, 1.3 eq., tetrakis(triphenylphosphine)palladium(0) (110 mg, 0.094 mmol, 0.05 eq.), potassium carbonate (1.0 g, 7.5 mmol, 4 eq.) and water (5 mL). The resulting biphasic suspension was vigorously de-oxygenated via sub-surface purging with nitrogen for 15 min. The reaction vessel was then sealed and heated at 95° C. for 16 h. After cooling to RT, the reaction suspension was added 10 mL of MeOH and 5 mL of 2 N aq. lithium hydroxide (10 mmol, 5.3 eq.). The resulting mixture was then heated at 60° C. for another 2.5 h. Finally, the reaction was quenched with 10% aq. HCl and extracted with ether. The combined organic extracts were washed further with water and brine, dried over Na$_2$SO$_4$, filtered and the filtrate concentrated in vacuo. Purification of the crude product thus obtained by way of reverse phase column chromatography (C$_{18}$, gradient elution, 9:1 (v/v) H$_2$O: MeCN+0.1% TFA→MeCN+0.1% TFA) afforded the title compound as a white solid (590 mg, 51% yield). LC-MS: 609 (M+H)$^+$.

Example 2

2-(4-ethoxy-4'-(3-(4-ethyl-5-oxo-1-(4-(trifluoromethyl)phenyl)-4,5-dihydro-1H-1,2,4-triazol-3-yl) propyl)-[1,1'-biphenyl]-3-yl)acetic acid

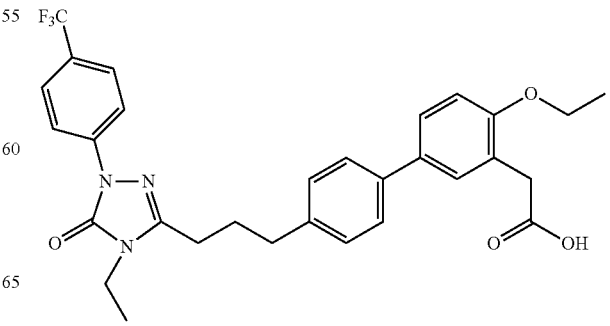

Prepared in an analogous manner to Example 1 but using instead ethyl isocyanate as the electrophile in step 1. LC-MS: 554 (M+H)+

Example 3

2-(4-ethoxy-4'-(3-(5-oxo-4-propyl-1-(4-(trifluoromethyl)phenyl)-4,5-dihydro-1H-1,2,4-triazol-3-yl)propyl)-[1,1'-biphenyl]-3-yl)acetic acid

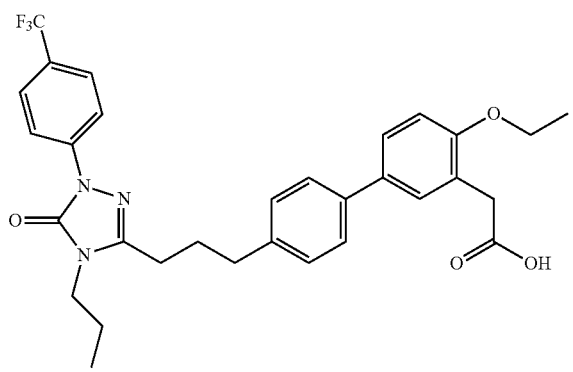 [SMILES: CCCn1c(CCCc2ccc(-c3ccc(OCC)c(CC(=O)O)c3)cc2)nn(-c2ccc(C(F)(F)F)cc2)c1=O]

Prepared in an analogous manner to Example 1 but using instead n-propyl isocyanate as the electrophile in step 1. LC-MS: 568 (M+H)+.

Example 4

2-(4'-(3-(4-cyclopentyl-5-oxo-1-(4-(trifluoromethyl)phenyl)-4,5-dihydro-1H-1,2,4-triazol-3-yl(propyl)-4-ethoxy-[1,1% biphenyl-]-3-yl)acetic acid

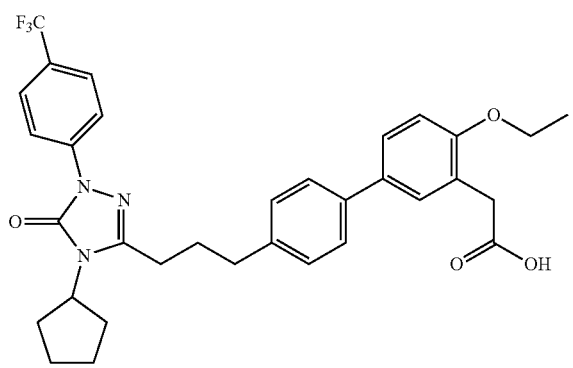 [SMILES: CCOc1ccc(-c2ccc(CCCc3nn(-c4ccc(C(F)(F)F)cc4)c(=O)n3C3CCCC3)cc2)cc1CC(=O)O]

Prepared in an analogous manner to Example 1 but using instead cyclopentyl isocyanate as the electrophile in step 1. LC-MS: 594 (M+H)+.

Example 5

2-(4-ethoxy-(4'-(3-(4-(4-methylcyclohexyl)-5-oxo-1-(4-(trifluoromethyl)phenyl)-4,5-dihydro-1H-1,2,4-triazol-3-yl)propyl)-[1,1'-biphenyl]-3-yl)acetic acid

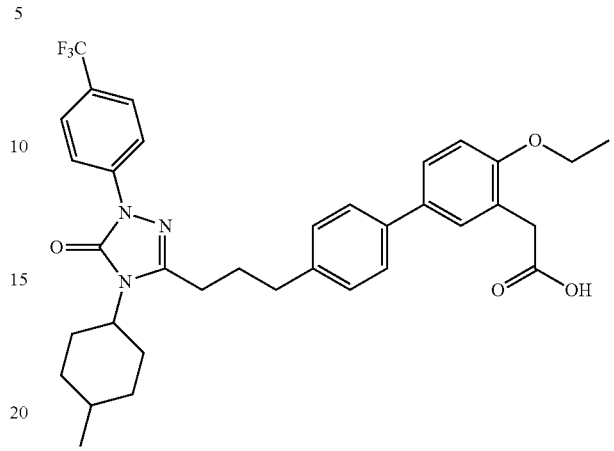

Prepared in an analogous manner to Example 1 but using instead 1-isocyanato-4-methylcyclohexane as the electrophile in step 1. LC-MS: 622 (M+H)+.

Example 6

2-(4-ethoxy-(4'-(3-(4-(3-methylcyclohexyl)-5-oxo-1-(4-(trifluoromethyl)phenyl)-4,5-dihydro-1H-1,2,4-triazol-3-yl)propyl)-[1,1'-biphenyl]-3-yl)acetic acid

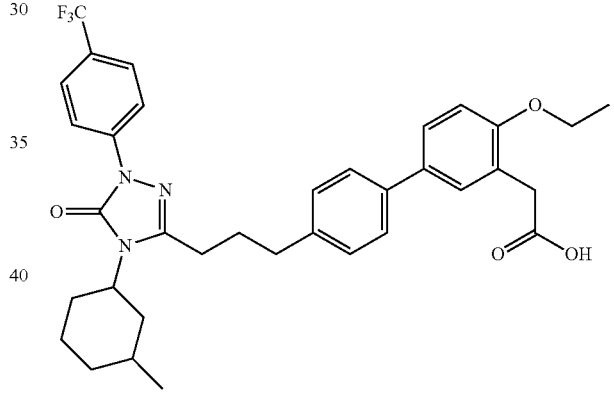

Prepared in an analogous manner to Example 1 but using instead 1-isocyanato-3-methylcyclohexane as the electrophile in step 1. LC-MS: 622 (M+H)+.

Example 7

2-(4-ethoxy-(4'-(3-(4-(2-methylcyclohexyl)-5-oxo-1-(4-(trifluoromethyl)phenyl)-4,5-dihydro-1H-1,2,4-triazol-3-yl)propyl)-[1,1'-biphenyl]-3-yl)acetic acid

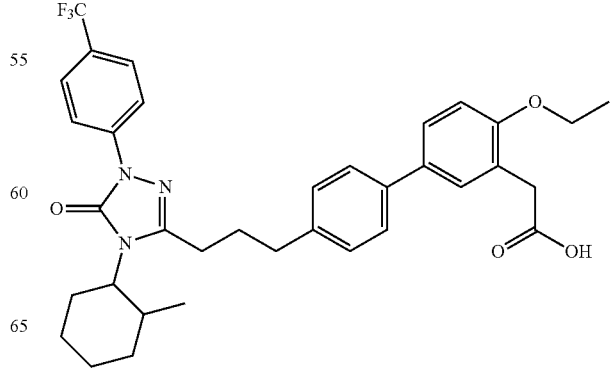

Prepared in an analogous manner to Example 1 but using instead 1-isocyanato-2-methylcyclohexane as the electrophile in step 1. LC-MS: 622 (M+H)+.

Example 8

2-(4'-(3-(4-cyclohexyl-5-oxo-1-(4-(trifluoromethoxy)phenyl)-4,5-dihydro-1H-1,2,4-triazol-3-yl)propyl)-4-ethoxy-[1,1% biphenyl]-3-yl)acetic acid

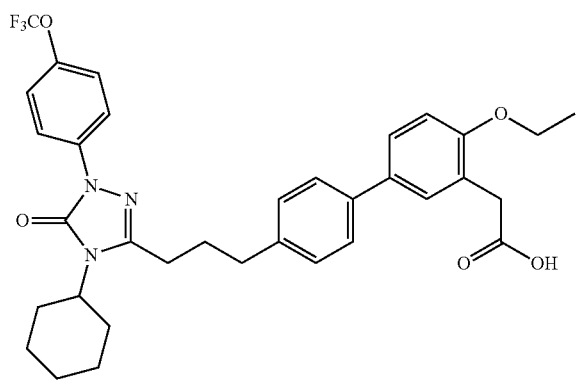 [SMILES: CCOc1ccc(-c2ccc(CCCc3nn(-c4ccc(OC(F)(F)F)cc4)c(=O)n3C3CCCCC3)cc2)cc1CC(=O)O]

Prepared in an analogous manner to Example 1 but using instead 1-iodo-4-(trifluoromethoxy)benzene as a coupling partner in step 3. LC-MS: 624 (M+H)+.

Example 9

2-(4-ethoxy-4'-(3-(4-(2-fluorophenyl)-5-oxo-1-(4-(trifluoromethyl)phenyl)-4,5-dihydro-1H-1,2,4-triazol-3-yl)propyl)-2'-methyl-[1,1% biphenyl]-3-yl) acetic acid

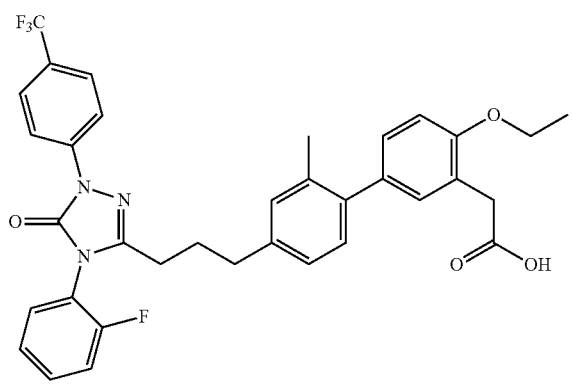 [SMILES: CCOc1ccc(-c2ccc(CCCc3nn(-c4ccc(C(F)(F)F)cc4)c(=O)n3-c3ccccc3F)cc2C)cc1CC(=O)O]

Prepared in an analogous manner to Example 1 but using instead 4-(4-bromo-3-methylphenyl)butanehydrazide and 2-fluorophenyl isocyanate as coupling partners in step 1. LC-MS: 634 (M+H)+.

Example 10

4'-(3-(4-(2-fluorophenyl)-5-oxo-1-(4-(trifluoromethyl)phenyl)-4,5-dihydro-1H-1,2,4-triazol-3-yl) propyl)-2'-methyl-(4-trifluoromethyl)-[1,1'-biphenyl-]-3-carboxylic acid

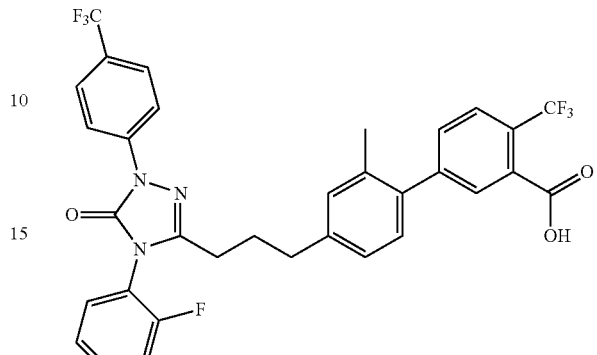

Prepared in an analogous manner to Example 1 but with the following modifications:
Step 1 was performed using 4-(4-bromo-3-methylphenyl) butanehydrazide and 2-fluorophenyl isocyanate as coupling partners.

After completion of Step 3, the resulting bromide was converted to the pinacol boronate as follows; To a solution of 3-(3-(4-bromo-3-methylphenyl)propyl)-4-(2-fluorophenyl)-1-(4-(trifluoromethyl)phenyl)-1H-1,2,4-triazol-5(4H)-one (300 mg, 0.56 mmol) in dioxane (6 mL) was added bis(pinacolato)diboron (171 mg, 0.67 mmpl), potassium acetate (166 mg, 1.68 mmol) and Pd(dppf)Cl$_2$. The resultant solution was sparged with nitrogen and heated at 90° C. for 16 hrs. After cooling to ambient temperature, the reaction mixture was diluted with EtOAc, washed with water, dried (MgSO$_4$), filtered and evaporated in vacuo. Purification of the residue using silica gel chromatography (0 to 80% EtOAc in hexanes gradient) afforded the corresponding boronate in 85% yield (275 mg).

Step 4: To the previously isolated boronate (92 mg, 0.158 mmol) in a mixture of DME (3 mL) and water (1 mL) was added 5-bromo-2-(trifluoromethyl)benzoic acid (51 mg, 0.19 mmol), K$_3$PO$_4$ (134 mg, 0.63 mmol), S-Phos (29 mg, 0.032 mmol) and Pd$_2$(dba)$_3$ (2 mg, 0.004 mmol). The solution was sparged with nitrogen for 5 minutes then heated to 90° C. for 20 hr after which the reaction mixture was evaporated and the residue purified by preparative HPLC to afford the title compound. LC-MS: 644 (M+H)+.

Example 11

4-ethoxy-4'-(3-(4-(2-fluorophenyl)-5-oxo-1-(4-(trifluoromethyl)phenyl)-4,5-dihydro-1H-1,2,4-triazol-3-yl)propyl)-2'-methyl-[1,1% biphenyl-]-3-carboxylic acid

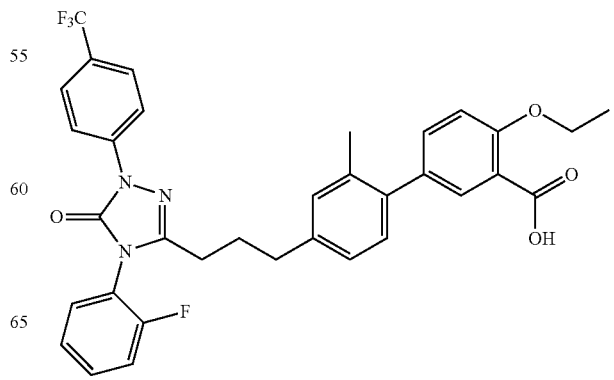

Prepared in an analogous manner to Example 1 but using instead 4-(4-bromo-3-methylphenyl)butanehydrazide and 2-fluorophenyl isocyanate as coupling partners in step 1, and ethyl 2-ethoxy-5-(4,4,5,5-tetramethyl-1,3,2-dioxaborolan-2-yl) as coupling partner in step 4. LC-MS: 620 (M+H)$^+$.

Example 12

2-(4-ethoxy-4'-((((4-(2-fluorophenyl)-5-oxo-1-(4-(trifluoromethyl)phenyl)-4,5-dihydro-1H-1,2,4-triazol-3-yl)methyl)amino)methyl)-[1,1'-biphenyl]-3-yl)acetic acid

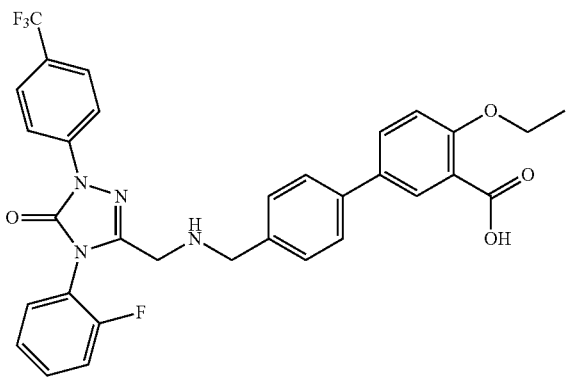 [SMILES: CCOc1ccc(-c2ccc(CNCc3nn(-c4ccc(C(F)(F)F)cc4)c(=O)n3-c3ccccc3F)cc2)cc1C(=O)O]

Step 1: To a dichloromethane (15 mL) suspension of (4-(2-fluorophenyl)-3-(hydroxymethyl)-1-(4-(trifluoromethyl)phenyl)-1H-1,2,4-triazol-5(4H)-one (1.0 g, 2.8 mmol, 1 eq., prepared according to procedure described in WO2008/103574) and sodium bicarbonate (360 mg, 4.2 mmol, 1.5 eq.) was added Dess-Martin periodinane (1.4 g, 3.4 mmol, 1.2 eq.) at 0° C. portion-wise over 10 min. The resulting mixture was allowed to warm slowly to room temperature over 5 h. The reaction was then quenched with the addition of 10% aq. Na$_2$S$_2$O$_3$ and extracted with ether. The combined organic extracts were then washed further with 1 N aq. NaOH, water and brine, dried over Na$_2$SO$_4$, and filtered. Concentration of the filtrate in vacuo afforded the desired product aldehyde as a colorless oil (0.49 g, 45% yield).

Step 2: To a dichloromethane (3 mL) solution of (4-(2-fluorophenyl)-5-oxo-1-(4-trifluoromethyl)phenyl)-4,5-dihydro-1H-1,2,4-triazole-3-carbaldehyde (0.10 g, 0.29 mmol, 1 eq.) from the previous step was added sequentially 4-iodobenzylamine (73 mg, 0.31 mmol, 1.1 eq.), acetic acid (0.025 mL, 0.43 mmol, 1.5 eq.), and sodium cyanoborohydride (27 mg, 0.43 mmol, 1.5 eq.). The resulting mixture was stirred at RT for 16 h. The reaction was then quenched with the addition of saturated aq. NaHCO$_3$ and extracted with EtOAc. The combined organic extracts were then washed further with 1 N aq. NaOH, water and brine, dried over Na$_2$SO$_4$, filtered and the filtrate concentrated in vacuo. Purification of the crude product thus obtained by way of column chromatography (SiO$_2$, gradient elution, 7:1 (v/v) Hex: EtOAc→EtOAc) afforded the desired product as a pale yellow oil (80 mg, 92% yield).

Step 3: To a dioxane (10 mL) solution of (4-(2-fluorophenyl)-34((4-iodobenzyl)amino)methyl)-1-(4-(trifluoromethyl)phenyl)-1H-1,2,4-triazol-5(4H)-one (80 mg, 0.14 mmol, 1 eq.) from the previous step was added methyl 2-(2-ethoxy-5-(4,4,5,5-tetramethyl-1,3,2-dioxaborolan-2-yl)phenyl)acetate (54 mg, 0.17 mmol, 1.3 eq., prepared according to procedure described in international patent application PCT/US2013/029713), tetrakis(triphenylphosphine)palladium(0) (16 mg, 0.014 mmol, 0.1 eq.), and saturated aq. sodium bicarbonate (1.5 mL). The resulting biphasic suspension was vigorously de-oxygenated via sub-surface purging with nitrogen for 15 min. The reaction vessel was then sealed and heated at 90° C. for 24 h. After cooling to RT, the volatiles were removed in vacuo and the resulting residue was back-extracted with EtOAc. The combined organic extracts were washed further with water and brine, dried over Na$_2$SO$_4$, filtered and the filtrate concentrated in vacuo. Purification of the crude product thus obtained by way of column chromatography (SiO$_2$, gradient elution, Hex→1:1:8 (v/v/v) Hex: MeOH: EtOAc) afforded the desired product as a pale yellow oil (80 mg, 90% yield).

Step 4: To a 2:1 (v/v) THF: MeOH (1 mL) solution of methyl 2-(4-ethoxy-4'-((((4-(2-fluorophenyl)-5-oxo-1-(4-(trifluoromethyl)phenyl)-4,5-dihydro-1H-1,2,4-triazol-3-yl)methyl)amino)methyl)-[1,1'-biphenyl]-3-yl)acetate (80 mg, 0.13 mmol, 1 eq.) from the previous step was added 2 N aq. lithium hydroxide (0.5 mL, 1 mmol, 7.7 eq.). The resulting solution was then stirred at RT until reaction was deemed to be complete as judged by LC-MS analysis. At this time, the reaction mixture was diluted with water and brought to pH of 4 with the addition of solid citric acid. The resulting suspension was then extracted with EtOAc. The combined organic extracts were washed further with water and brine, dried over MgSO$_4$, and filtered. Concentration of the filtrate in vacuo furnished the title compound as a colorless oil. LC-MS: 621 (M+H)$^+$.

Example 13

N-(6-(4-(3-(5-oxo-4-propyl-1-(4-(trifluoromethyl)phenyl)-4,5-dihydro-1H-1,2,4-triazol-3-yl)propyl)phenyl)pyridin-2-yl)benzenesulfonamide

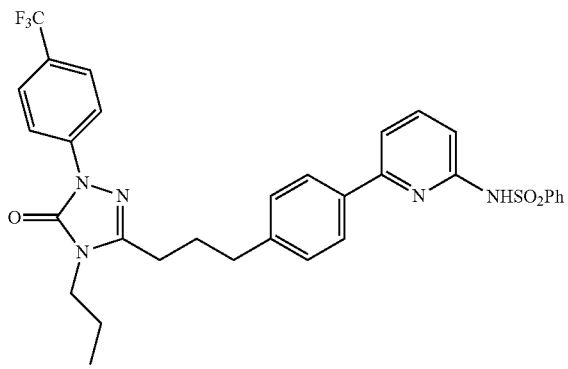

Step 1: To a dioxane (5 mL) solution of 3-(3-(4-bromophenyl)propyl)-4-propyl-1-(4-(trifluoromethyl)phenyl)-1H-1,2,4-triazol-5(4H)-one (0.44 g, 0.98 mmol, 1 eq.) from Example 3, step 3 was added potassium acetate (0.29 g, 2.9 mmol 3 eq.), bis(pinacolato)diboron (0.30 g, 1.2 mmol, 1.2 eq.) and [1,1'-bis(diphenylphosphino)ferrocene]dichloropalladium(II) (72 mg, 0.098 mmol, 0.1 eq.). The resulting solution was vigorously de-oxygenated via sub-surface purging with nitrogen for 15 min. The reaction vessel was then sealed and heated at 90° C. for 16 h. After cooling to RT, the reaction mixture was diluted with ether and washed sequentially with water and brine. The organic extract was then dried over Na$_2$SO$_4$, filtered and the filtrate concentrated in vacuo. Purification of the crude product thus obtained by way of column chromatography (SiO$_2$, gradient elution, Hex→1:8 (v/v) Hex: EtOAc) afforded desired product as a pale yellow oil that solidified upon standing (240 mg, 50% yield).

Step 2: To a DME (2 mL) solution of 4-propyl-3-(3-(4-(4,4,5,5-tetramethyl-1,3,2-dioxaborolan-2-yl)phenyl)propyl)-1-(4-(trifluoromethyl)phenyl)-1H-1,2,4-triazol-5(4H)-one (81 mg, 0.16 mmol, 1 eq.) from the previous step was added 2-amino-6-bromopyridine (33 mg, 0.19 mmol, 1.2 eq), tetrakis(triphenylphosphine)palladium(0) (19 mg, 0.016 mmol, 0.1 eq.), and saturated aq. sodium bicarbonate (1.5 mL). The resulting biphasic suspension was vigorously de-oxygenated via sub-surface purging with nitrogen for 15 min. The reaction vessel was then sealed and heated at 90° C. for 16 h. After cooling to RT, the volatiles were removed in vacuo and the resulting residue was directly subjected to column chromatography (SiO$_2$, gradient elution, Hex→1: 1:8 (v/v/v) Hex: MeOH: EtOAc) afforded the desired product as a pale yellow oil (77 mg, 99% yield).

Step 3: To a pyridine (2 mL) solution of 3-(3-(4-(6-aminopyridin-2-yl)phenyl)propyl)-4-propyl-1-(4-(trifluoromethyl)phenyl)-1H-1,2,4-triazol-5(4H)-one (74 mg, 0.16 mmol) was added benzene sulfonyl chloride (23 µL, 0.17 mmol, 1.1 eq) and the resulting solution was stirred at RT for 16 h. The mixture thus obtained was diluted with dichloromethane and washed sequentially with saturated aq. CuSO$_4$, water and brine. The organic extract was then dried over Na$_2$SO$_4$, filtered and the filtrate concentrated in vacuo. The crude product thus obtained was then purified by prep HPLC (gradient elution: 7:3 (v/v) H$_2$O: MeCN+0.1% TFA→MeCN+0.1% TFA) to afford the title compound as a white solid. LC-MS: 622 (M+H)$^+$.

Example 14

2-(4'-(3-(4-cyclopropyl-5-oxo-1-(4-(trifluoromethyl)phenyl)-4,5-dihydro-1H-1,2,4-triazol-3-yl)propyl)-4-methoxy-[1,1'-biphenyl]-3-yl)acetic acid

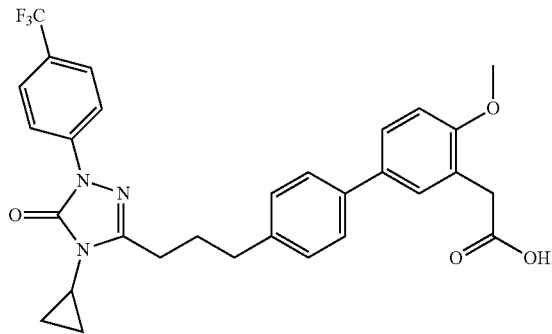 [SMILES: COc1ccc(-c2ccc(CCCc3nn(-c4ccc(C(F)(F)F)cc4)c(=O)n3C3CC3)cc2)cc1CC(=O)O]

Step 1: To a THF (60 mL) solution of 4-(4-bromophenyl) butanehydrazide (2.9 g, 11.3 mmol) was added cyclopropyl isocyanate (940 mg, 11.3 mmol) The resulting solution was allowed to stir at RT for 18 h, becoming a thick white suspension. This mixture was then evaporated to dryness and used in the next step without further purification.

Step 2: The previously isolated hydrazide was suspended in MeOH (50 mL) and potassium hydroxide (6.7 g) added. The suspension was heated to reflux for 16 h after which the solution was evaporated, the residue diluted in DCM (100 mL) and slowly made acidic with 1N HCl (aq.). The organic phase was separated, the aqueous phase extracted with DCM and the combined organic phases dried (MgSO$_4$), filtered and evaporated in vacuo. The residue was purified on silica gel eluting with a gradient of hexanes:EtOAc (0 to 100%) to afford 3-(3-(4-bromophenyl)propyl)-4-cyclopropyl-1H-1,2,4-triazol-5(4H)-one as a colorless solid.

Step 3: To a solution of 3-(3-(4-bromophenyl)propyl)-4-cyclopropyl-1H-1,2,4-triazol-5(4H)-one (2.32 g, 7.20 mmol) in dioxane (40 mL) was added trans-N,N'-dimethylcyclohexane-1,2-diamine (113 µL, 0.72 mmol), potassium carbonate (2.0 g, 14.4 mmol), 4-iodobenzotrifluoride (2.15 g, 7.90 mmol) and CuI (69 mg, 0.36 mmol). The resulting suspension was heated to reflux under nitrogen for 16 h after which the suspension was evaporated in vacuo and the resulting mixture diluted with EtOAc and washed with water. The organic phase was dried (MgSO$_4$), filtered, evaporated in vacuo and the residue purified on silica gel eluting with a gradient of 0 to 30% EtOAc in hexanes to afford 3-(3-(4-bromophenyl)propyl)-4-cyclopropyl-1-(4-(trifluoromethyl)phenyl)-1H-1,2,4-triazol-5(4H)-one as a colorless solid.

Step 4: The previously isolated triazolone (250 mg, 0.54 mmol) was dissolved in dioxane (4 mL) to which was added methyl 2-(2-methoxy-5-(4,4,5,5-tetramethyl-1,3,2-dioxaborolan-2-yl)phenyl)acetate; 170 mg, 0.56 mmol) and sat'd aq. NaHCO$_3$ (2 mL). The solution was degassed via subsurface purge with nitrogen gas and Pd(PPh$_3$)$_4$ (~15 mg) added and heated in a sealed vial at 85° C. for 3 h. After complete reaction as judged by LCMS analysis, the solution was partitioned between EtOAc and water, the organic phase separated, dried (MgSO$_4$), filtered and evaporated in vacuo. The residue was purified on silica gel eluting with a gradient of 0 to 40% EtOAc in hexanes to afford the desired ester.

Step 5: Methyl 2-(4'-(3-(4-cyclopropyl-5-oxo-1-(4-(trifluoromethyl)phenyl)-4,5-dihydro-1H-1,2,4-triazol-3-yl) propyl)-4-methoxy-[1,1'-biphenyl]-3-yl)acetate (150 mg, 0.27 mmol) was dissolved in a mixture of THF (3 mL), MeOH (1 ml) and water (1 mL) to which was added lithium hydroxide monohydrate (60 mg, 1.43 mmol). This mixture was stirred at RT until hydrolysis of the ester was judged complete by LCMS analysis. The reaction mixture was diluted with water and EtOAc to which solid citric acid was added until the aqueous phase became acidic. The organic phase was separated, washed with water, dried (MgSO$_4$), filtered and evaporated in vacuo to afford the title compound as a colorless solid. LC-MS: 552 (M+H)$^+$.

Example 15

2-(4'-(3-(4-(2-fluorobenzyl)-5-oxo-1-(4-(trifluoromethyl)phenyl)-4,5-dihydro-1H-1,2,4-triazol-3-yl) propyl)-4-methoxy-[1,1'-biphenyl]-3-yl)acetic acid

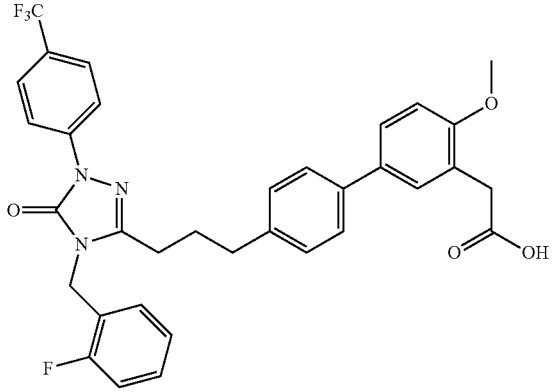 [SMILES: COc1ccc(-c2ccc(CCCc3nn(-c4ccc(C(F)(F)F)cc4)c(=O)n3Cc3ccccc3F)cc2)cc1CC(=O)O]

Prepared in an analogous manner to Example 14 but using 2-fluorobenzyl isocyanate as the electrophile in step 1. LC-MS: 620 (M+H)⁺.

Example 16

2-(4-ethoxy-4'-(3-(4-(2-fluorobenzyl)-5-oxo-1-(4-(trifluoromethyl)phenyl)-4,5-dihydro-1H-1,2,4-triazol-3-yl)propyl)-[1,1'-biphenyl-]-3-yl)acetic acid

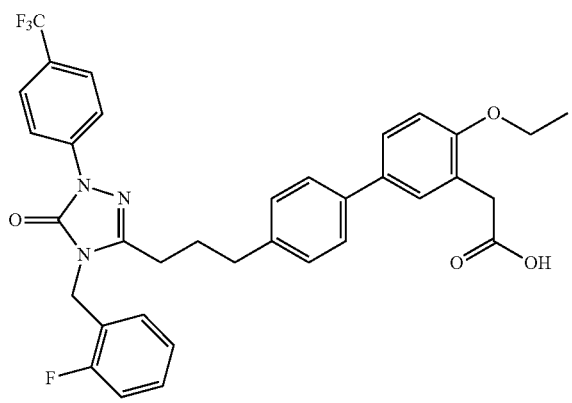 [SMILES: CCOc1ccc(-c2ccc(CCCc3nn(-c4ccc(C(F)(F)F)cc4)c(=O)n3Cc3ccccc3F)cc2)cc1CC(=O)O]

Prepared in an analogous manner to Example 14 but using 2-fluorobenzyl isocyanate as the electrophile in step 1 and methyl 2-(2-ethoxy-5-(4,4,5,5-tetramethyl-1,3,2-dioxaborolan-2-yl)phenyl)acetate as the coupling partner in step 4. LC-MS: 634 (M+H)⁺.

Example 17

2-(4'-(3-(4-cyclopropyl-5-oxo-1-(4-(trifluoromethyl)phenyl)-4,5-dihydro-1H-1,2,4-triazol-3-yl)propyl)-4-propoxy-[1,1'-biphenyl-]-3-yl)acetic acid

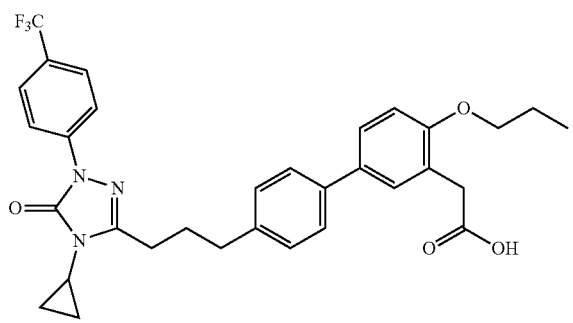 [SMILES: CCCOc1ccc(-c2ccc(CCCc3nn(-c4ccc(C(F)(F)F)cc4)c(=O)n3C3CC3)cc2)cc1CC(=O)O]

Prepared in an analogous manner to Example 14 but using methyl 2-(2-propoxy-5-(4,4,5,5-tetramethyl-1,3,2-dioxaborolan-2-yl)phenyl)acetate as the coupling partner in step 4. LC-MS: 580 (M+H)⁺.

Example 18

2-(4-ethoxy-4'-(3-(5-oxo-4-phenyl-1-(4-(trifluoromethyl)phenyl)-4,5-dihydro-1H-1,2,4-triazol-3-yl)propyl-[1,1'-biphenyl-]-3-yl)acetic acid

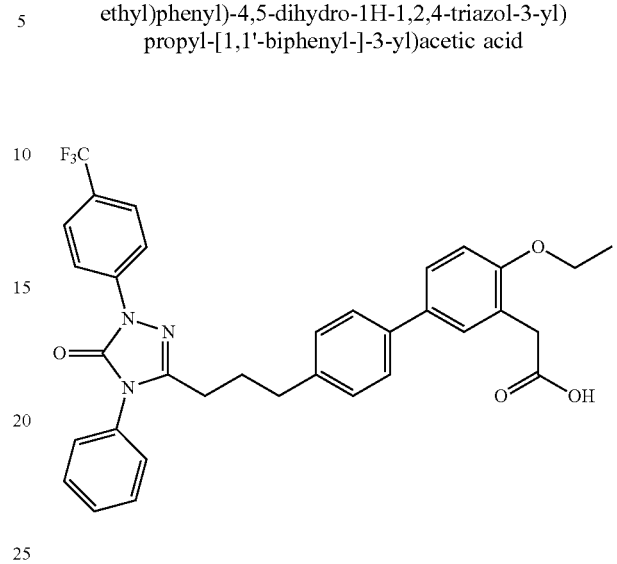

Prepared in an analogous manner to Example 14 but using phenyl isocyanate as the electrophile in step 1 and methyl 2-(2-ethoxy-5-(4,4,5,5-tetramethyl-1,3,2-dioxaborolan-2-yl)phenyl)acetate as the coupling partner in step 4. LC-MS: 602 (M+H)⁺.

Example 19

2-(4'-(3-(4-(2-chlorophenyl)-5-oxo-1-(4-(trifluoromethyl)phenyl)-4,5-dihydro-1H-1,2,4-triazol-3-yl)propyl-4-ethoxy-[1,1'-biphenyl-]-3-yl)acetic acid

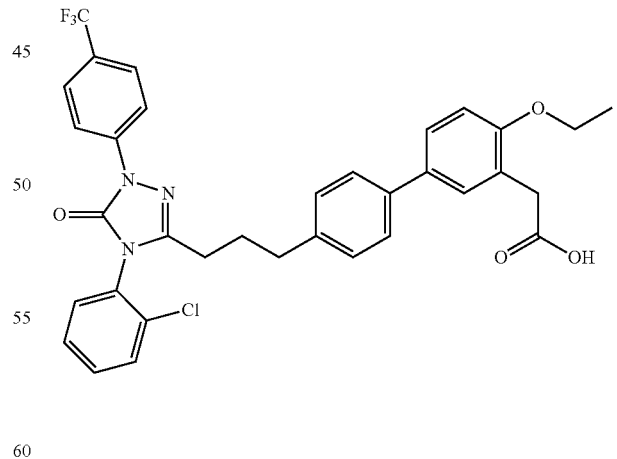

Prepared in an analogous manner to Example 14 but using 2-chlorophenyl isocyanate as the electrophile in step 1 (using cyclization procedure from Example 1) and methyl 2-(2-ethoxy-5-(4,4,5,5-tetramethyl-1,3,2-dioxaborolan-2-yl)phenyl)acetate as the coupling partner in step 4. LC-MS: 637 (M+H)⁺.

Example 20

2-(4-ethoxy-4'-(3-(4-isobutyl-5-oxo-1-(4-(trifluoromethyl)phenyl)-4,5-dihydro-1H-1,2,4-triazol-3-yl)propyl-[1,1'-biphenyl-]-3-yl)acetic acid

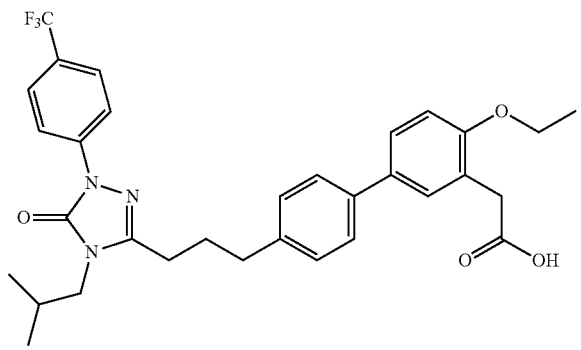 [SMILES: CCOc1ccc(-c2ccc(CCCc3nn(-c4ccc(C(F)(F)F)cc4)c(=O)n3CC(C)C)cc2)cc1CC(=O)O]

Prepared in an analogous manner to Example 14 but using 1-isocyanato-2-methylpropane as the electrophile in step 1 and methyl 2-(2-ethoxy-5-(4,4,5,5-tetramethyl-1,3,2-dioxaborolan-2-yl)phenyl)acetate as the coupling partner in step 4. LC-MS: 582 (M+H)$^+$.

Example 21

2-(4-ethoxy-4'-(3-(4-(3-fluorophenyl)-5-oxo-1-(4-(trifluoromethyl)phenyl)-4,5-dihydro-1H-1,2,4-triazol-3-yl)propyl-[1,1'-biphenyl-]-3-yl)acetic acid

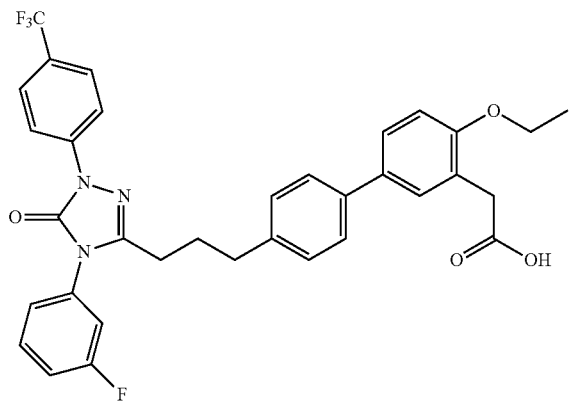 [SMILES: CCOc1ccc(-c2ccc(CCCc3nn(-c4ccc(C(F)(F)F)cc4)c(=O)n3-c3cccc(F)c3)cc2)cc1CC(=O)O]

Prepared in an analogous manner to Example 14 but using 3-fluorophenyl isocyanate as the electrophile in step 1 (using cyclization procedure from Example 1) and methyl 2-(2-ethoxy-5-(4,4,5,5-tetramethyl-1,3,2-dioxaborolan-2-yl)phenyl)acetate as the coupling partner in step 4. LC-MS: 620 (M+H)$^+$.

Example 22

2-(4'-(3-(4-(2,5-difluorophenyl)-5-oxo-1-(4-(trifluoromethyl)phenyl)-4,5-dihydro-1H-1,2,4-triazol-3-yl)propyl-4-ethoxy-[1,1'-biphenyl-]-3-yl)acetic acid

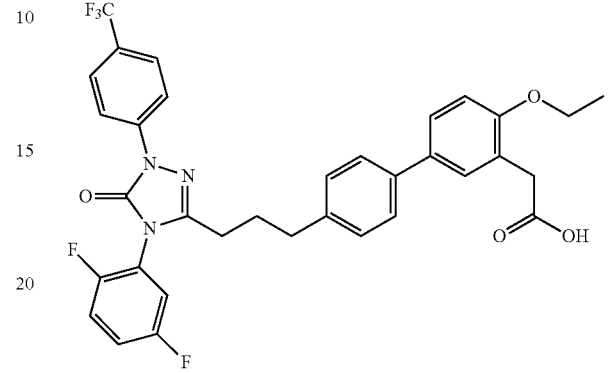

Prepared in an analogous manner to Example 14 but using 2,5-difluorophenyl isocyanate as the electrophile in step 1 (using cyclization procedure from Example 1) and methyl 2-(2-ethoxy-5-(4,4,5,5-tetramethyl-1,3,2-dioxaborolan-2-yl)phenyl)acetate as the coupling partner in step 4. LC-MS: 638 (M+H)$^+$.

Example 23

2-(4'-(3-(4-(2,6-difluorophenyl)-5-oxo-1-(4-(trifluoromethyl)phenyl)-4,5-dihydro-1H-1,2,4-triazol-3-yl)propyl-4-ethoxy-[1,1'-biphenyl-]-3-yl)acetic acid

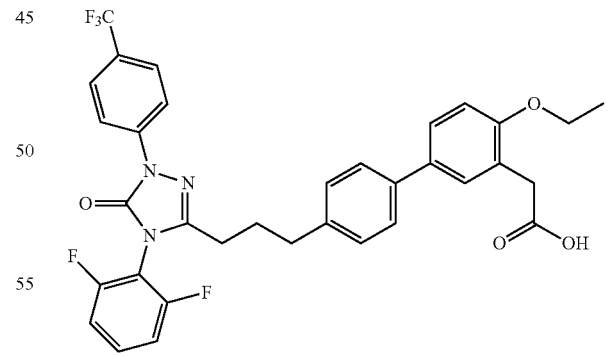

Prepared in an analogous manner to Example 14 but using 2,6-difluorophenyl isocyanate as the electrophile in step 1 (using cyclization procedure from Example 1) and methyl 2-(2-ethoxy-5-(4,4,5,5-tetramethyl-1,3,2-dioxaborolan-2-yl)phenyl)acetate as the coupling partner in step 4. LC-MS: 638 (M+H)$^+$.

Example 24

2-(4'-(3-(4-(4-(tert-butyl)phenyl)-5-oxo-1-(4-(trifluoromethyl)phenyl)-4,5-dihydro-1H-1,2,4-triazol-3-yl)propyl-4-ethoxy-[1,1'-biphenyl]-3-yl)acetic acid

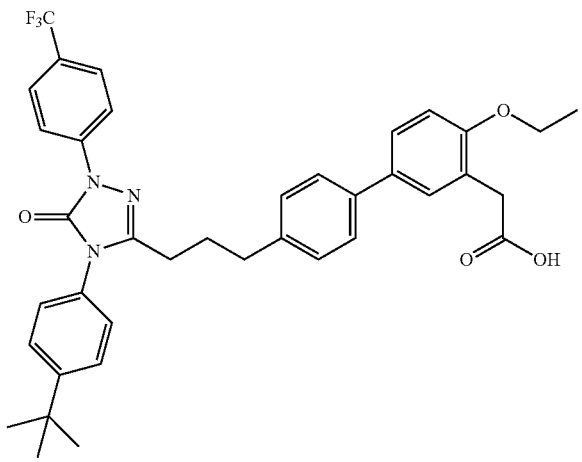 [SMILES: CCOc1ccc(-c2ccc(CCCc3nn(-c4ccc(C(F)(F)F)cc4)c(=O)n3-c3ccc(C(C)(C)C)cc3)cc2)cc1CC(=O)O]

Prepared in an analogous manner to Example 14 but using 4-tert-butylphenyl isocyanate as the electrophile in step 1 (using cyclization procedure from Example 1) and methyl 2-(2-ethoxy-5-(4,4,5,5-tetramethyl-1,3,2-dioxaborolan-2-yl)phenyl)acetate as the coupling partner in step 4. LC-MS: 658 (M+H)+.

Example 25

2-(4-ethoxy-4'-(3-(4-(2-ethylphenyl)-5-oxo-1-(4-(trifluoromethyl)phenyl)-4,5-dihydro-1H-1,2,4-triazol-3-yl)propyl)-[1,1'-biphenyl]-3-yl)acetic acid

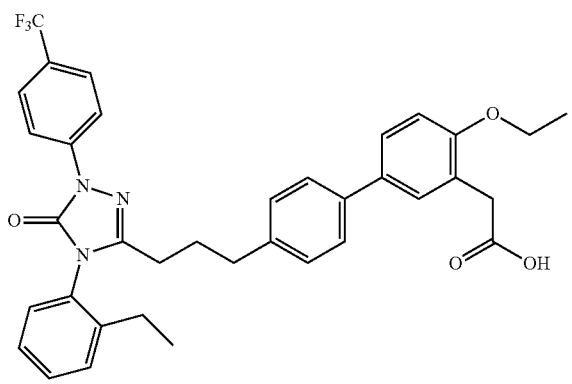 [SMILES: CCOc1ccc(-c2ccc(CCCc3nn(-c4ccc(C(F)(F)F)cc4)c(=O)n3-c3ccccc3CC)cc2)cc1CC(=O)O]

Prepared in an analogous manner to Example 14 but using 2-ethylphenyl isocyanate as the electrophile in step 1 (using cyclization procedure from Example 1) and methyl 2-(2-ethoxy-5-(4,4,5,5-tetramethyl-1,3,2-dioxaborolan-2-yl)phenyl)acetate as the coupling partner in step 4. LC-MS: 630 (M+H)+.

Example 26

2-(4-ethoxy-4'-(3-(4-(2-methoxyphenyl)-5-oxo-1-(4-(trifluoromethyl)phenyl)-4,5-dihydro-1H-1,2,4-triazol-3-yl)propyl-[1,1'-biphenyl-]-3-yl)acetic acid

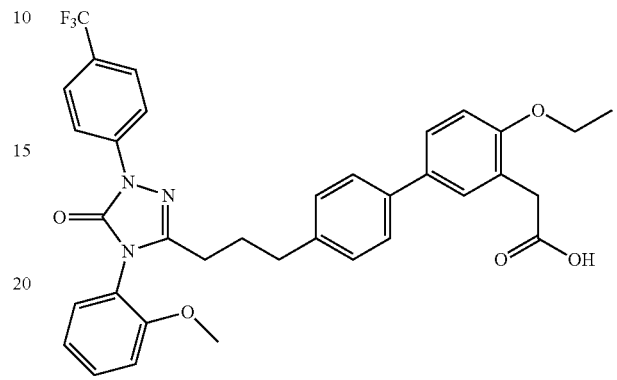

Prepared in an analogous manner to Example 14 but using 2-methoxylphenyl isocyanate as the electrophile in step 1 (using cyclization procedure from Example 1) and methyl 2-(2-ethoxy-5-(4,4,5,5-tetramethyl-1,3,2-dioxaborolan-2-yl)phenyl)acetate as the coupling partner in step 4. LC-MS: 632 (M+H)+.

Example 27

2-(4'-(3-(4-(2-chlorophenyl)-1-(4-isopropylphenyl)-5-oxo-4,5-dihydro-1H-1,2,4-triazol-3-yl)propyl)-4-ethoxy-[1,1'-biphenyl-]-3-yl)acetic acid

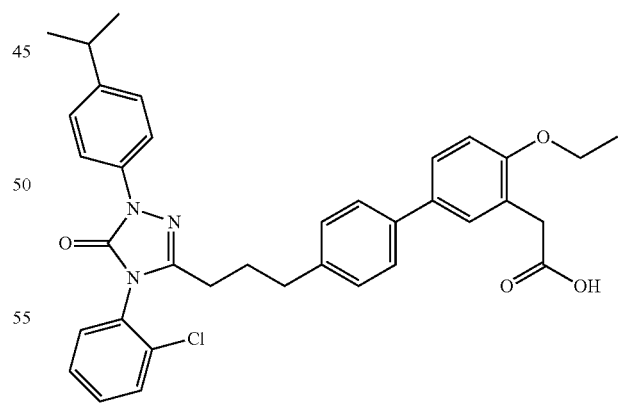

Prepared in an analogous manner to Example 14 but using 2-chlorophenyl isocyanate as the electrophile in step 1 (using cyclization procedure from Example 1), 1-iodo-4-isopropylbenzene as the coupling partner in step 3 and methyl 2-(2-ethoxy-5-(4,4,5,5-tetramethyl-1,3,2-dioxaborolan-2-yl)phenyl)acetate as the coupling partner in step 4. LC-MS: 611 (M+H)+.

Example 28

2-(4'-(3-(1-(4-(tert-butyl)phenyl)-4-(2,6-dichlorophenyl)-5-oxo-4,5-dihydro-1H-1,2,4-triazol-3-yl)propyl-4-ethoxy-[1,1'-biphenyl]-3-yl)acetic acid

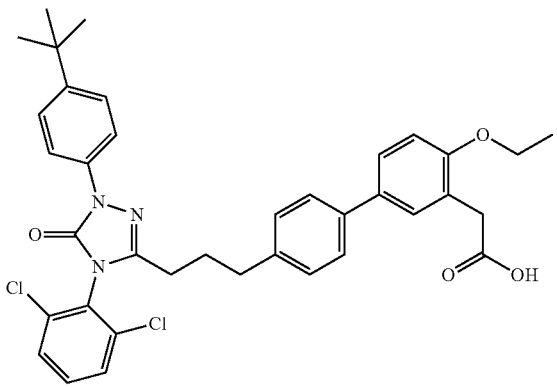 [SMILES: CCOc1ccc(-c2ccc(CCCc3nn(-c4ccc(C(C)(C)C)cc4)c(=O)n3-c3c(Cl)cccc3Cl)cc2)cc1CC(=O)O]

Prepared in an analogous manner to Example 14 but using 2,6-dichlorophenyl isocyanate as the electrophile in step 1 (using cyclization procedure from Example 1), 4-tert-butyliodobenzene as the coupling partner in step 3 and methyl 2-(2-ethoxy-5-(4,4,5,5-tetramethyl-1,3,2-dioxaborolan-2-yl)phenyl)acetate as the coupling partner in step 4. LC-MS: 659 (M+H)$^+$.

Example 29

2-(4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-yl)acetic acid

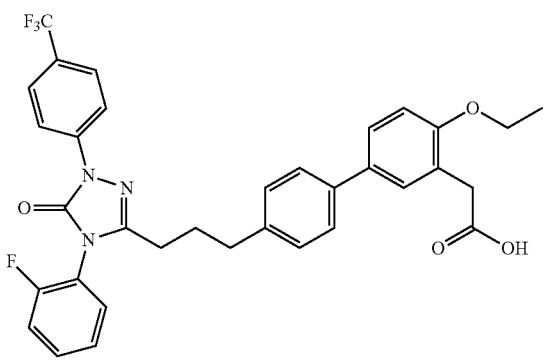 [SMILES: CCOc1ccc(-c2ccc(CCCc3nn(-c4ccc(C(F)(F)F)cc4)c(=O)n3-c3ccccc3F)cc2)cc1CC(=O)O]

Step 1; To a solution of 4-(4-bromophenyl)butanehydrazide (1.00 g, 3.89 mmol) in anhydrous THF (25 mL) at 0° C. was added 2-fluorophenyl isocyanate (0.48 mL, 4.28 mmol). The resulting mixture was stirred slowly to RT for 16 h. The solvents were evaporated and the resulting white solid was suspended in 1:4 Et$_2$O/hexanes, sonicated, and filtered. The solid containing 2-(4-(4-bromophenyl)butanoyl)-N-(2-fluorophenyl)hydrazinecarboxamide was used directly in the next step.

Step 2; To a suspension of 2-(4-(4-bromophenyl)butanoyl)-N-(2-fluorophenyl)hydrazinecarboxamide (1.50 g, 3.80 mmol) in toluene (40 mL) and TEA (2.63 mL, 19.00 mmol) was added TMSOTf (2.06 mL, 11.41 mmol). The resulting mixture was stirred at reflux for 16 h. The reaction was cooled to RT and diluted with EtOAc and sat. aq. NaHCO$_3$. The organic phase was then washed sequentially with water, brine, filtered through a Na$_2$SO$_4$/paper plug and concentrated in vacuo. The crude 3-(3-(4-bromophenyl)propyl)-4-(2-fluorophenyl)-1H-1,2,4-triazol-5(4H)-one was used directly in the next step.

Step 3; A stirring mixture of 3-(3-(4-bromophenyl)propyl)-4-(2-fluorophenyl)-1H-1,2,4-triazol-5(4H)-one (0.44 g, 1.17 mmol), potassium carbonate (0.323 g, 2.34 mmol), 4-trifluoromethyliodobenzene (0.323 mL, 2.34 mmol), and dioxane (15 mL) was sub-surface purged with nitrogen gas for 5 minutes before adding copper(I) iodide (0.011 g, 0.06 mmol), 1,2-trans-dimethylaminocyclohexane (0.014 mL, 0.117 mmol). The reaction vessel was refluxed for 16 h, cooled to RT, and diluted with ether and sat. aq. NaHCO$_3$. The organic extract was washed sequentially with water (2×) and concentrated in vacuo. The resulting crude material was purified on silica gel eluting with a solvent gradient of 0% to 40% EtOAc in hexanes to afford 3-(3-(4-bromophenyl)propyl)-4-(2-fluorophenyl)-1-(4-(trifluoromethyl)phenyl)-1H-1,2,4-triazol-5 (4H)-one.

Step 4; To a solution of 3-(3-(4-bromophenyl)propyl)-4-(2-fluorophenyl)-1-(4-(trifluoromethyl)phenyl)-1H-1,2,4-triazol-5(4H)-one (0.080 g, 0.154 mmol) in dioxane (3 mL) was added methyl 2-(2-ethoxy-5-(4,4,5,5-tetramethyl-1,3,2-dioxaborolan-2-yl)phenyl)acetate (0.052 g, 0.161 mmol) and sat. aq. NaHCO$_3$ (1 mL). The resulting mixture was sparged with nitrogen gas for 5 minutes before tetrakis(triphenylphosphine)palladium(0) (0.018 g, 0.0154 mmol) was added. The reaction vessel was then sealed and heated at 85° C. for 16 h. The reaction mixture was allowed to cool to RT then partitioned between EtOAc and brine. The organic phase was extracted once with water and concentrated in vacuo. The residue thus obtained was purified using a preparatory TLC plate using 30% EtOAc in hexanes as eluent to afford methyl 2-(4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-yl)acetate.

Step 5; To a stirring mixture of methyl 2-(4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-yl)acetate (0.033 g, 0.052 mmol) in THF (1.5 mL) and MeOH (1.5 mL) was added lithium hydroxide (1.0 M in H$_2$O, 0.52 mL, 0.52 mmol) and 1.0 mL of H$_2$O. The solution was stirred at 50° C. for 16 h, evaporated, and partitioned between EtOAc and 1N HCl (to pH~1). The organic phase was extracted with H$_2$O (2×) and concentrated in vacuo to afford the title compound. LC-MS: 620 (M+H)$^+$.

Example 30

2-(4-ethoxy-3'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-yl)acetic acid

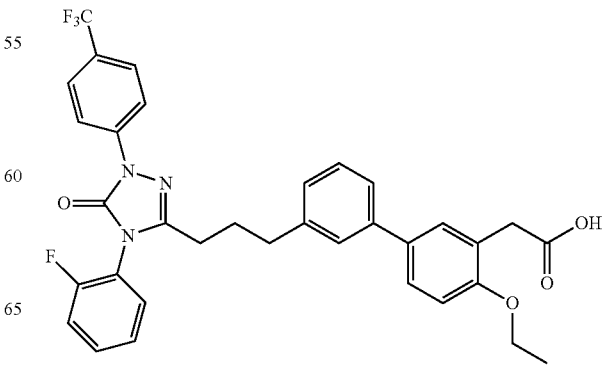

Prepared in an analogous manner to Example 29 using 4-(3-bromophenyl)butanehydrazide in step 1. LC-MS: 620 (M+H)⁺.

Example 31

2-(4-ethoxy-3'-(3-(4-isopropyl-5-oxo-1-(4-(trifluoromethyl)phenyl)-4,5-dihydro-1H-1,2,4-triazol-3-yl)propyl-[1,1'-biphenyl]-3-yl)acetic acid

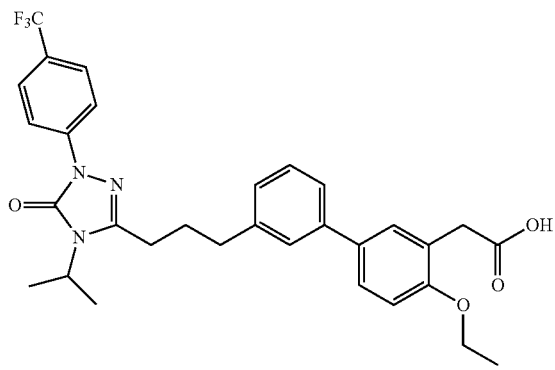 [SMILES: CCOc1ccc(-c2cccc(CCCc3nn(-c4ccc(C(F)(F)F)cc4)c(=O)n3C(C)C)c2)cc1CC(=O)O]

Prepared in an analogous manner to Example 29 using isopropyl isocyanate and 4-(3-bromophenyl)butanehydrazide in step 1. LC-MS: 567 (M+H)⁺.

Example 32

4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-carboxylic acid

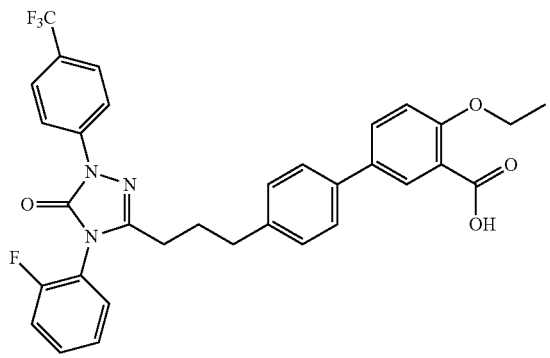 [SMILES: CCOc1ccc(-c2ccc(CCCc3nn(-c4ccc(C(F)(F)F)cc4)c(=O)n3-c3ccccc3F)cc2)cc1C(=O)O]

Step 1; To a solution of 3-(3-(4-bromophenyl)propyl)-4-(2-fluorophenyl)-1-(4-(trifluoromethyl)phenyl)-1H-1,2,4-triazol-5(4H)-one (0.330 g, 0.725 mmol, Example 29, step 4) in p-dioxane (10 mL) was added potassium acetate (0.244 g, 2.18 mmol), bis(pinacolato)diboron (0.274 g, 0.942 mmol) and Pd(dppf)Cl₂ (0.060 g, 0.073 mmol). The solution was sub-surface purged with nitrogen gas for 5 minutes, then heated at 85° C. under a nitrogen atmosphere for 16 h. The dark reaction was allowed to cool, partly evaporated, and partitioned between EtOAc and Brine. The organic phase was washed once with H₂O and evaporated in vacuo. The residue was purified on silica gel eluting with a gradient of 0 to 40% EtOAc in hexanes to afford 4-(2-fluorophenyl)-3-(3-(4-(4,4,5,5-tetramethyl-1,3,2-dioxaborolan-2-yl)phenyl)propyl)-1-(4-(trifluoromethyl)phenyl)-1H-1,2,4-triazol-5(4H)-one.

Step 2; To a solution of 4-(2-fluorophenyl)-3-(3-(4-(4,4,5,5-tetramethyl-1,3,2-dioxaborolan-2-yl)phenyl) propyl)-1-(4-(trifluoromethyl)phenyl)-1H-1,2,4-triazol-5(4H)-one (0.065 g, 0.154 mmol) in dioxane (3 mL) was added methyl 5-bromo-2-ethoxybenzoate (0.033 g, 0.126 mmol) and sat. aq. NaHCO₃ (1 mL). The resulting mixture was sparged with nitrogen gas for 5 minutes before tetrakis(triphenylphosphine) palladium(0) (0.014 g, 0.0115 mmol) was added. The reaction vessel was then sealed and heated at 90° C. for 16 h. The reaction mixture was allowed to cool to RT and partitioned between EtOAc and brine. The organic phase was extracted once with water and concentrated in vacuo. The residue thus obtained was purified using a preparatory TLC plate using 25% acetone in hexanes as eluent to afford methyl 4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-carboxylic acid ester.

Step 3; To a mixture of methyl 4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-carboxylic acid ester (0.047 g, 0.052 mmol) in THF (2.0 mL) and MeOH (2.0 mL) was added lithium hydroxide (1.0 M in H₂O, 0.78 mL, 0.78 mmol) and 1.2 mL of H₂O. The solution was stirred at 60° C. for 16 h, evaporated, and partitioned between EtOAc and 1N HCl (to pH~1). The organic phase was extracted with H₂O (2×) and concentrated in vacuo to afford the title compound. LC-MS: 606 (M+H)⁺.

Example 33

2-(4-ethoxy-4'-(3-(4-(2-fluorophenyl)-5-oxo-1-(2-chloro-4-(trifluoromethyl)phenyl)-4,5-dihydro-1H-1,2,4-triazol-3-yl)propyl)-[1,1'-biphenyl]-3-yl)acetic acid

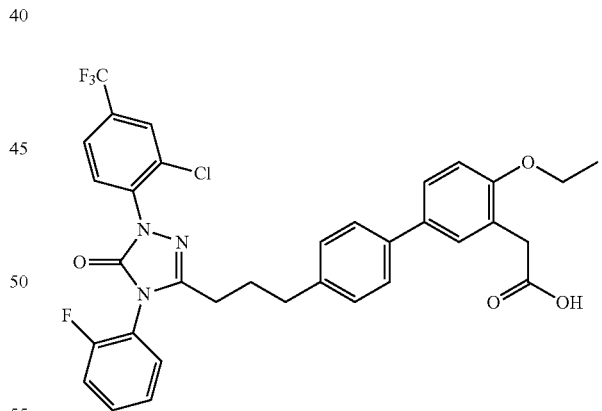

Step 1; A stirring mixture of 3-(3-(4-bromophenyl)propyl)-4-(2-fluorophenyl)-1H-1,2,4-triazol-5(4H)-one (0.200 g, 0.53 mmol, Example 29, step 3), copper(I) iodide (0.010 g, 0.053 mmol), potassium carbonate (0.147 g, 1.06 mmol), L-proline (0.012 g, 0.106 mmol) and DMSO (5 mL) was sub-surface purged with nitrogen gas for 10 minutes before adding 2-chloro-4-trifluoromethyliodobenzene (0.103 mL, 0.58 mmol). The reaction vessel was stirred at 90° C. for 48 h, cooled to RT, and diluted with ether and brine. The organic extract was washed sequentially with 1N HCl (aq.) and water. The organic layer was then concentrated in vacuo.

The resulting crude material was purified on silica gel eluting with a solvent gradient of 0% to 45% EtOAc in hexanes to afford 3-(3-(4-bromophenyl)propyl)-4-(2-fluorophenyl)-1-(2-chloro-4-(trifluoromethyl)phenyl)-1H-1,2,4-triazol-5(4H)-one.

The title compound was prepared in an analogous manner to Example 29 using 3-(3-(4-bromophenyl)propyl)-4-(2-fluorophenyl)-1-(2-chloro-4-(trifluoromethyl)phenyl)-1H-1,2,4-triazol-5 (4H)-one in step 4. LC-MS: 655 (M+H)$^+$.

Example 34

2-(4-ethoxy-4'-(3-(4-(2-fluorophenyl)-5-oxo-1-(3-(trifluoromethyl)phenyl)-4,5-dihydro-1H-1,2,4-triazol-3-yl)propyl)-[1,1'-biphenyl]-3-yl)acetic acid

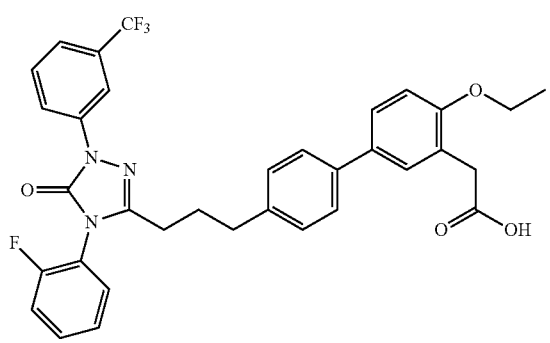 [SMILES: CCOc1ccc(-c2ccc(CCCc3nn(-c4cccc(C(F)(F)F)c4)c(=O)n3-c3ccccc3F)cc2)cc1CC(=O)O]

Prepared in an analogous manner to Example 29 using 3-trifluoromethyliodobenzene in step 3. LC-MS: 620 (M+H)$^+$.

Example 35

2-(4-ethoxy-4'-(3-(4-(2-(trifluoromethyl)phenyl)-5-oxo-1-(4-(trifluoromethyl)phenyl)-4,5-dihydro-1H-1,2,4-triazol-3-yl)propyl)-[1,1'-biphenyl]-3-yl)acetic acid

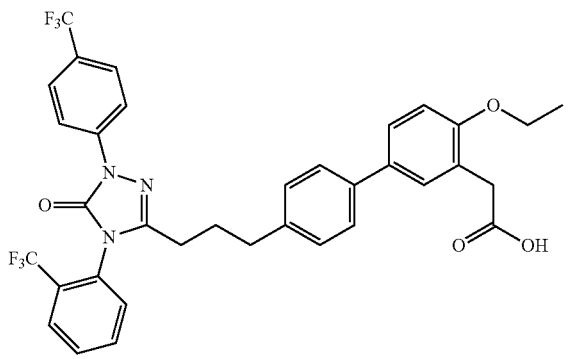 [SMILES: CCOc1ccc(-c2ccc(CCCc3nn(-c4ccc(C(F)(F)F)cc4)c(=O)n3-c3ccccc3C(F)(F)F)cc2)cc1CC(=O)O]

Prepared in an analogous manner to Example 29 using 2-(trifluoromethyl)phenyl isocyanate in step 1. LC-MS: 670 (M+H)$^+$.

Example 36

2-(4-ethoxy-4'-(3-(1-(2-fluorophenyl)-5-oxo-4-(4-(trifluoromethyl)phenyl)-4,5-dihydro-1H-1,2,4-triazol-3-yl)propyl)-[1,1'-biphenyl]-3-yl)acetic acid

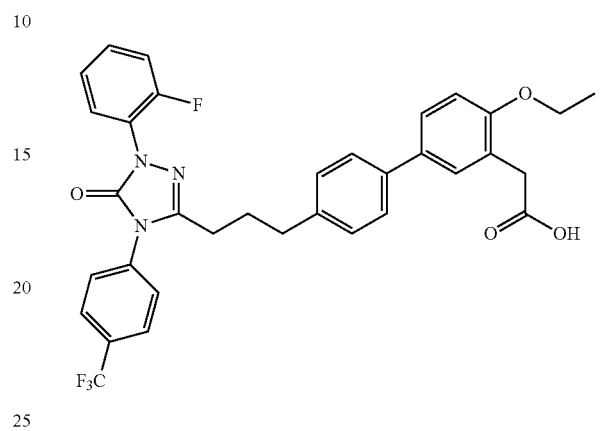

Prepared in an analogous manner to Example 29 using 4-(trifluoromethyl)phenyl isocyanate in step 1 and using 2-fluoroiodobenzene with conditions described in Example 33, step 1. LC-MS: 620 (M+H)$^+$.

Example 37

2-(4-ethoxy-4'-(3-(1-(4-(trifluoromethyl)phenyl)-5-oxo-4-(4-(trifluoromethyl)phenyl)-4,5-dihydro-1H-1,2,4-triazol-3-yl)propyl-[1,1'-biphenyl-]-3-yl)acetic acid Prepared in an analogous manner to Example 29 using 4-(trifluoromethyl)phenyl isocyanate in step 1. LC-MS: 670 (M+H)$^+$.

Example 38

2-(4-ethoxy-4'-(3-(5-oxo-4-(pyridin-2-yl)-1-(4-(trifluoromethyl)phenyl)-4,5-dihydro-1H-1,2,4-triazol-3-yl)propyl-[1,1'-biphenyl-]-3-yl)acetic acid

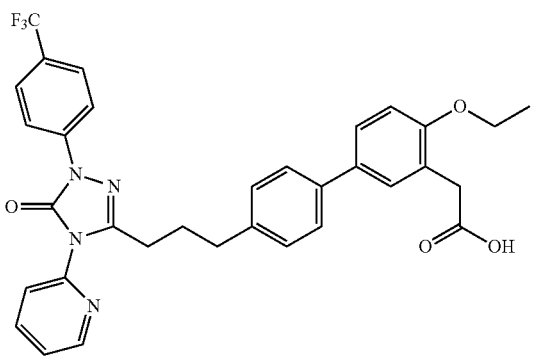 [SMILES: CCOc1ccc(-c2ccc(CCCc3nn(-c4ccc(C(F)(F)F)cc4)c(=O)n3-c3ccccn3)cc2)cc1CC(=O)O]

Step 1; To a stirring solution of 2-picolinic acid (1.00 g, 8.0 mmol) in toluene (25 mL) was added diphenylphosphoryl azide (2.00 mL, 9.34 mmol) and triethylamine (1.35 mL, 9.74 mmol). The resulting mixture was stirred at RT for 1.5 h, 80° C. for 3 h, then cooled to RT. The resulting suspension was filtered, rinsing with a minimal amount of EtOAc first, then hexanes. The gray solid containing 2-isocyanatopyridine was used directly in the next step.

Step 2; To a solution of 4-(4-bromophenyl)butanehydrazide (0.620 g, 2.41 mmol) in DMF (15 mL) at RT was added 2-isocyanatopyridine (0.347 g, 2.89 mmol). The resulting mixture was stirred at 90° C. for 16 h. The solvents were evaporated and the resulting residue was treated with Et$_2$O, sonicated, and resulting suspension was filtered. The solid containing 2-(4-(4-bromophenyl)butanoyl)-N-(pyridin-2-yl)hydrazinecarboxamide was used directly in the next step.

The title compound was prepared in an analogous manner to Example 29 using 2-(4-(4-bromophenyl)butanoyl)-N-(pyridin-2-yl)hydrazinecarboxamide in step 2. LC-MS: 603 (M+H)$^+$.

Example 39

2-(4-propoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl-]-3-yl)acetic acid

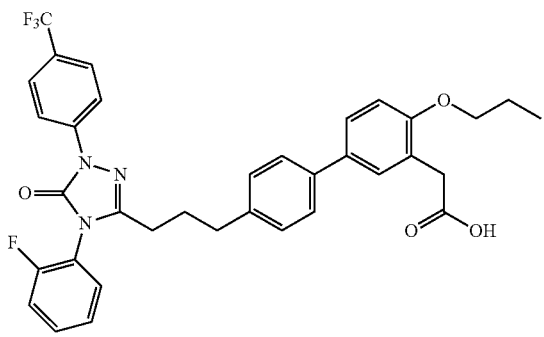 [SMILES: CCCOc1ccc(-c2ccc(CCCc3nn(-c4ccc(C(F)(F)F)cc4)c(=O)n3-c3ccccc3F)cc2)cc1CC(=O)O]

Prepared in an analogous manner to Example 29 using methyl 2-(2-propoxy-5-(4,4,5,5-tetramethyl-1,3,2-dioxaborolan-2-yl)phenyl)acetate in step 4. LC-MS: 634 (M+H)$^+$.

Example 40

2-(4-ethoxy-4'-(3-(5-oxo-4-(o-tolyl)-1-(4-(trifluoromethyl)phenyl)-4,5-dihydro-1H-1,2,4-triazol-3-yl)propyl)-[1,1'-biphenyl]-3-yl)acetic acid

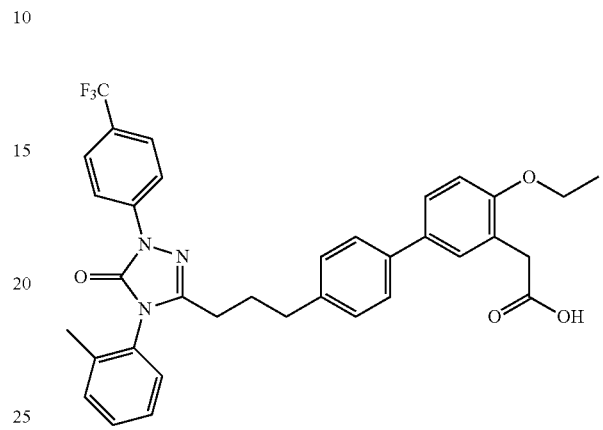

Prepared in an analogous manner to Example 29 using 1-isocyanato-2-methylbenzene in step 1. LC-MS: 616 (M+H)$^+$.

Example 41

2-(4-ethoxy-4'-(3-(5-oxo-4-(pyridin-3-yl)-1-(4-(trifluoromethyl)phenyl)-4,5-dihydro-1H-1,2,4-triazol-3-yl)propyl-[1,1'-biphenyl-]-3-yl)acetic acid

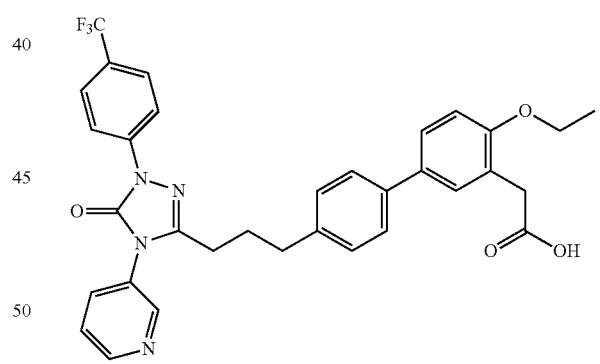

Prepared in an analogous manner to Example 39 using nicotinic acid in step 1. LC-MS: 603 (M+H)$^+$.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula Ib

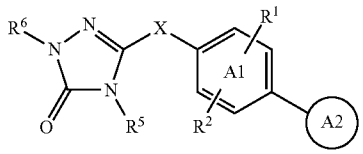

or a pharmaceutically acceptable salt thereof wherein:
A1 is phenyl;
A2 is A2a

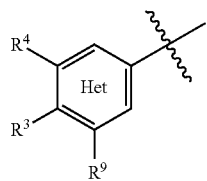

wherein A2 is phenyl or pyridine;
X is —(CH$_2$)$_m$—, wherein m is 2, 3 or 4;
R$^1$, R$^2$ and R$^9$ are each independently selected from the group consisting of hydrogen, halogen, —CF$_3$, and —C$_{1-6}$alkyl;
R$^3$ is selected from the group consisting of:
(a) hydrogen,
(b) halogen,
(c) —CN,
(d) —CF$_3$,
(e) —C$_{1-6}$alkyl,
(f) —C$_{1-6}$alkyl-C(=O)OH,
(g) —O—(R$^8$), and
(h) —N(R$^7$)(R$^8$),
wherein the alkyl portion of choices (e) and (f) are optionally substituted with halogen, oxo or hydroxyl;
R$^4$ is selected from the group consisting of:
(a) hydrogen,
(b) —N(R$^7$)S(=O)$_2$R$^8$,
(c) —O—R$^8$,
(d) —C$_{1-6}$alkyl-C(=O)OH, and
(e) —C(=O)OH,
with the proviso that at least one of R$^3$ and R$^4$ is other than hydrogen;
R$^5$ is selected from the group consisting of:
(a) —C$_{1-6}$alkyl,
(b) —C$_{1-4}$alkyl(R$^7$),
(c) —aryl,
(d) —heteroaryl, and
(e) —C$_{3-6}$cycloalkyl,
wherein the alkyl portion of choices (a) and (b) is optionally substituted with halogen, the cycloalkyl portion of choice (e) is optionally substituted with halogen or —C$_{1-6}$alkyl, and wherein the aryl of choice (c) and the heteroaryl of choice (d) are optionally mono- or di-substituted with substituents selected from the group consisting of halogen, —C$_{1-6}$alkyl, —CF$_3$,—C$_{1-6}$alkoxy, haloC$_{1-6}$alkyl, —C$_{3-6}$cycloalkyl, and —C$_{3-6}$cycloalkoxy;
R$^6$ is aryl, optionally mono- or di-substituted with substituents selected from the group consisting of halogen, nitro, —CF$_3$, —OCF$_3$, —C$_{1-6}$alkyl, —C$_{1-6}$alkoxy, and haloC$_{1-6}$alkyl;

R$^7$ and R$^8$ are each independently selected from the group consisting of:
(a) hydrogen,
(b) —C$_{1-6}$alkyl,
(c) —C$_{3-6}$cycloalkyl,
(d) aryl, and
(e) heteroaryl,
wherein the alkyl portion of choice (b) and the cycloalkyl portion of choice (c) are each optionally mono-, di- or tri-substituted with halogen, hydroxyl, —C$_{1-6}$alkyl, —C$_{1-6}$alkoxy, —C$_{3-6}$cycloalkyl or —C$_{3-6}$cycloalkoxy, and wherein the aryl portion of choice (d) and the heteroaryl portion of choice (e) are each optionally mono- or di-substituted with substituents selected from the group consisting of halogen, —C$_{1-6}$alkyl, —C$_{1-6}$ alkyl, haloC$_{1-6}$alkyl, —C$_{3-6}$cycloalkyl, —C$_{3-6}$cycloalkoxy, —C(=O)C$_{1-4}$alkyl, hydroxyl, CN, and —(C=O)OH.

2. A compound according to claim 1 or a pharmaceutically acceptable salt thereof wherein:
R$^1$, R$^2$ and R$^9$ are each independently selected from the group consisting of: hydrogen, halogen, and —C$_{1-6}$alkyl;
R$^3$ is selected from the group consisting of:
(a) hydrogen,
(b) —CF$_3$,
(c) —C$_{1-4}$alkyl, and
(d) —O—(R$^8$),
wherein the alkyl portion of choice (c) is optionally substituted with halogen, oxo or hydroxyl;
R$^4$ is selected from the group consisting of:
(a) hydrogen,
(b) —O—(R$^8$),
(c) —C$_{1-6}$alkyl-C(=O)OH,
and
(d) —C(=O)OH,
R$^5$ is selected from the group consisting of:
(a) —C$_{1-6}$alkyl,
(b) —C$_{1-4}$alkyl(R$^7$),
(c) —aryl,
(d) —heteroaryl, and
(e) —C$_{3-6}$cycloalkyl,
wherein the alkyl portion of choices (a) and (b) is optionally substituted with halogen, the cycloalkyl portion of choice (e) is optionally substituted with C$_{1-6}$alkyl, and wherein the aryl of choice (c) and the heteroaryl of choice (d) are optionally mono- or di-substituted with substituents selected from the group consisting of halogen, —C$_{1-6}$alkyl, —CF$_3$, —C$_{1-6}$alkoxy, haloC$_{1-6}$alkyl, —C$_{3-6}$cycloalkyl, and —C$_{3-6}$cycloalkoxy;
R$^7$ and R$^8$ are each independently selected from the group consisting of:
(a) hydrogen,
(b) —C$_{1-6}$alkyl, and
(c) aryl, and
wherein the alkyl portion of choice (b) is optionally mono-, di- or tri-substituted with halogen, hydroxyl, —C$_{1-6}$alkyl, —C$_{1-6}$alkoxy, —C$_{3-6}$cycloalkyl or —C$_{3-6}$ cycloalkoxy, wherein the aryl portion of choice (c) is optionally mono- or di-substituted with substituents selected from the group consisting of halogen, —C$_{1-6}$alkyl, —C$_{1-6}$alkoxy, haloC$_{1-6}$alkyl, —C$_{3-6}$cycloalkyl, and —(C=O)OH.

3. The compound according to claim 2, or a pharmaceutically acceptable salt thereof, wherein X is —CH$_2$CH$_2$CH$_2$—.

4. The compound according to claim 2, or a pharmaceutically acceptable salt thereof, wherein: $R^1$, $R^2$ and $R^9$ are each independently selected from the group consisting of:
hydrogen and methyl.

5. A compound according to claim 1, or a pharmaceutically acceptable salt thereof, wherein: $R^3$ is selected from the group consisting of:
(a) hydrogen,
(b) —$CF_3$,
(c) —$C_{1-4}$alkyl, and
(d) —O—($R^8$),
wherein the alkyl portion of choice (c) is optionally substituted with halogen, oxo or hydroxyl.

6. The compound according to claim 5, or a pharmaceutically acceptable salt thereof, wherein: $R^3$ is selected from the group consisting of: hydrogen and —O—($R^8$).

7. The compound according to claim 2, or a pharmaceutically acceptable salt thereof, wherein: $R^4$ is selected from the group consisting of:
(a) hydrogen,
(b) —$C_{1-6}$alkyl-C(=O)OH, and
(c) —C(=O)OH.

8. The compound according to claim 7, or a pharmaceutically acceptable salt thereof, wherein: $R^4$ is selected from the group consisting of:
(a) hydrogen, and
(b) —$CH_2$—C(=O)OH.

9. The compound according to claim 2 or a pharmaceutically acceptable salt thereof, wherein: $R^5$ is selected from the group consisting of:
(a) —$C_{1-4}$alkyl,
(b) pyridinyl,
(c) phenyl, and
(d) —$C_{3-6}$cycloalkyl,
wherein the cycloalkyl portion of choice (d) is optionally substituted with methyl, and wherein the pyridinyl of choice (b) and the phenyl of choice (c) are optionally mono- or di-substituted with substituents selected from the group consisting of halogen, —$C_{1-6}$alkyl, —$CF_3$, $C_{1-6}$alkoxy and halo$C_{1-6}$alkyl.

10. The compound according to claim 2 or a pharmaceutically acceptable salt thereof, wherein: $R^6$ is aryl, optionally mono- or di-substituted with halogen, —$CF_3$ or —$C_{1-4}$alkyl.

11. The compound according to claim 10 or a pharmaceutically acceptable salt thereof, wherein: $R^6$ is phenyl optionally mono- substituted with halogen, —$CF_3$, or —$C_{1-4}$ alkyl.

12. The compound according to claim 2 or a pharmaceutically acceptable salt thereof, wherein: $R^7$ is selected from hydrogen and methyl; and $R^8$ is selected from hydrogen, $C_{1-4}$alkyl optionally substituted with halogen, and phenyl optionally mono or di-substituted with substituents selected from the group consisting of halogen, —$C_{1-6}$alkyl, —$C_{1-6}$alkoxy, and halo$C_{1-6}$alkyl.

13. The compound according to claim 1 of Formula Ib

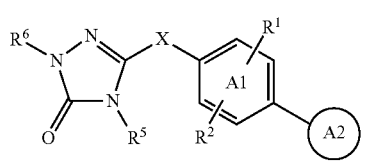

or a pharmaceutically acceptable salt thereof, wherein:
X is —$CH_2CH_2CH_2$—;
A1 is phenyl;
A2 is

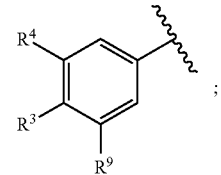

$R^1$, $R^2$ and $R^9$ are each independently selected from the group consisting of
(a) hydrogen,
(b) —$CF_3$, and
(c) —$C_{1-6}$alkyl;
$R^3$ is selected from the group consisting of:
(a) hydrogen,
(b) —$CF_3$,
(c) —$C_{1-4}$alkyl, and
(d) —O—($R^8$),
wherein the alkyl portion of choice (c) is optionally substituted with halogen, oxo or hydroxyl;
$R^4$ is selected from the group consisting of:
(a) hydrogen,
(b) —N($R^7$)S(=O)$_2R^8$,
(c) —$C_{1-6}$alkyl-C(=O)OH, and
(d) —C(=O)OH;
$R^5$ is selected from the group consisting of:
(a) —$C_{1-4}$alkyl,
(b) heteroaryl,
(c) phenyl, and
(d) —$C_{3-6}$cycloalkyl,
wherein the cycloalkyl portion of choice (d) is optionally substituted with methyl, and wherein the heteroaryl of choice (b) and the phenyl of choice (c) are optionally mono- or di-substituted with substituents selected from the group consisting of halogen, —$C_{1-6}$alkyl, —$CF_3$, —$C_{1-6}$alkoxy and halo$C_{1-6}$alkyl;
$R^6$ is aryl optionally mono- or di-substituted with —$CF_3$;
$R^7$ is selected from hydrogen and methyl; and
$R^8$ is selected from hydrogen, —$C_{1-4}$alkyl optionally substituted with halogen, and phenyl optionally mono or di-substituted with substituents selected from the group consisting of halogen, —$C_{1-6}$alkyl, —$C_{1-6}$alkoxy, and halo$C_{1-6}$alkyl.

14. The compound according to claim 1 of Formula Ib

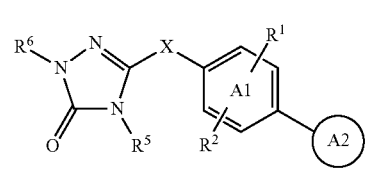

or a pharmaceutically acceptable salt thereof, wherein:
X is —$CH_2CH_2CH_2$—;
A1 is phenyl;
A2 is

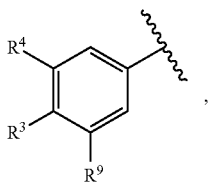

R¹, R² and R⁹ are each independently selected from the group consisting of:
(a) hydrogen, and
(b) methyl;

R³ is selected from the group consisting of:
(a) hydrogen,
(b) —CF₃, and
(c) —O—(R⁸);

R⁴ is selected from the group consisting of:
(a) hydrogen, and
(b) —CH₂—C(=O)OH;

R⁵ is selected from the group consisting of:
(a) —C₁₋₄alkyl,
(b) pyridinyl,
(c) phenyl, and
(d) —C₃₋₆cycloalkyl, wherein the cycloalkyl portion of choice (d) is optionally substituted with methyl, and wherein the pyridinyl of choice (b) and the phenyl of choice (c) are optionally mono- or di-substituted with substituents selected from the group consisting of halogen, —C₁₋₆alkyl, —CF₃, —C₁₋₆alkoxy and haloC₁₋₆alkyl;

R⁶ is phenyl optionally mono-substituted with —CF₃;

R⁸ is selected from hydrogen, —C₁₋₄alkyl optionally substituted with halogen, and phenyl optionally mono or di-substituted with substituents selected from the group consisting of halogen, —C₁₋₆alkyl, —C₁₋₆alkoxy, and haloC₁₋₆alkyl.

15. The compound according to claim 2 of Formula Ic

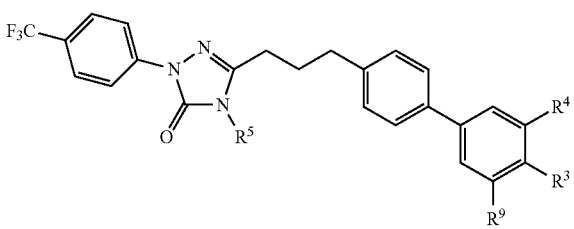

or is a pharmaceutically acceptable salt thereof.

16. The compound according to claim 15 wherein R⁹ is hydrogen.

17. The compound according to claim 1 selected from the group consisting of:

2-(4'-(3-(4-cyclohexyl-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4-ethoxy-4'-(3-(4-ethyl-5-oxo-1-(4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(5-oxo-4-propyl-1-(4-(trifluoromethyl)phenyl)-4,5-dihydro-1H-1,2,4-triazol-3-yl)propyl)-[1,1'-biphenyl]-3-yl)acetic acid, 2-(4'-(3-(4-cyclopentyl-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4-ethoxy-(4'-(3-(4-(4-methylcyclohexyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4-ethoxy-(4'-(3-(4-(3-methylcyclohexyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4-ethoxy-(4'-(3-(4-(2-methylcyclohexyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4'-(3-(4-cyclohexyl-5-oxo-1-(4-(trifluoromethoxy)phenyl)-4,5-dihydro-1H-1,2,4-triazol-3-yl)propyl)-4-ethoxy-[1,1'-biphenyl]-3-yl)acetic acid, 2-(4-ethoxy-4'-(3-(4-(2-fluorophenyl)-5-oxo-1-(4-(trifluoromethyl)phenyl)-4,5-dihydro-1H-1,2,4-triazol-3-yl)propyl)-2'-methyl-[1,1'-biphenyl]-3-yl)acetic acid, 4'-(3-(4-(2-fluorophenyl)-5-oxo-1-(4-(trifluoromethyl)phenyl)-4,5-dihydro-1H-1,2,4-triazol-3-yl)propyl)-2'-methyl-(4-trifluoromethyl)-,[1,1'-biphenyl]-3-carboxylic acid, 4-ethoxy-4'-(3-(4-(2-fluorophenyl)-5-oxo-1-(4-(trifluoromethyl)phenyl)-4,5-dihydro-1H-1,2,4-triazol-3-yl)propyl)-2'-methyl-[1,1'-biphenyl]-3-carboxylic acid, 2-(4-ethoxy-4'-((((4-(2-fluorophenyl)-5-oxo-1-(4-(trifluoromethyl)phenyl)-4,5-dihydro-1H-1,2,4-triazol-3-yl)methyl)amino)methyl)-[1,1'-biphenyl]-3-yl)acetic acid, N-(6-(4-(3-(5-oxo-4-propyl-1-(4-(trifluoromethyl)phenyl)-4,5-dihydro-1H-1,2,4-triazol-3-yl)propyl)phenyl)pyridin-2-yl)benzenesulfonamide, 2-(4'-(3-(4-cyclopropyl-5-oxo-1-(4-(trifluoromethyl)phenyl)-4,5-dihydro-1H-1,2,4-triazol-3-yl)propyl)-4-methoxy-[1,1'-biphenyl]-3-yl)acetic acid, 2-(4'-(3-(4-(2-fluorobenzyl)-5-oxo-1-(4-(trifluoromethyl)phenyl)-4,5-dihydro-1H-1,2,4-triazol-3-yl)propyl)-4-methoxy-[1,1'-biphenyl]-3-yl)acetic acid, 2-(4-ethoxy-4'-(3-(4-(2-fluorobenzyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4'-(3-(4-cyclopropyl-5-oxo-1-(4-(trifluoromethyl)phenyl)-4,5-dihydro-1H-1,2,4-triazol-3-yl)propyl)-4-propoxy-[1,1'-biphenyl]-3-yl)acetic acid, 2-(4-ethoxy-4'-(3-(5-oxo-4-phenyl-1-(4-(trifluoromethyl)phenyl)-4,5-dihydro-1H-1,2,4-triazol-3-yl)propyl),[1,1'-biphenyl]-3-yl)acetic acid, 2-(4'-(3-(4-(2-chlorophenyl)-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4-ethoxy-4'-(3-(4-isobutyl-5-oxo-1-(4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(4-(3-fluorophenyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4'-(3-(4-(2,5-difluorophenyl)-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4'-(3-(4-(2,6-difluorophenyl)-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4'-(3-(4-(4-(tert-butyl)phenyl)-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4-ethoxy-4'-(3-(4-(2-ethylphenyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(4-(2-methoxyphenyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4'-(3-(4-(2-chlorophenyl)-1-(4-isopropylphenyl)-5-oxo-4,5-dihydro-1H-1,2,4-triazol-3-yl)propyl)-4-ethoxy-[1,1'-biphenyl]-3-yl)acetic acid, 2-(4'-(3-(1-(4-(tert-butyl)phenyl)-4-(2,6-dichlorophenyl)-5-oxo-4,5-dihydro-1H-1,2,4-triazol-3-yl)propyl)-4-ethoxy-[1,1'-biphenyl]-3-yl)acetic acid, 2-(4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-yl)acetic acid, 4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-carboxylic acid, 2-(4-ethoxy-4'-(3-(4-(2-fluorophenyl)-5-oxo-1-(2-chloro-4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(4-(2-fluorophenyl)-5-oxo-1-(3-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(4-(2-(trifluoromethyl)phenyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(1-(2-fluorophenyl)-5-oxo-4-(4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(1-(4-(trifluoromethyl)phenyl)-5-oxo-4-(4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(5-oxo-4-(pyridin-2-yl)-1-(4-(trifluoromethyl)phenyl)-4,5-dihydro-1H-1,2,4-triazol-3-yl)propyl)-[1,1'-biphenyl]-3-yl)acetic acid, 2-(4-propoxy-4'-(3-(4-(2-fluorophenyl)-5-oxo-1-(4-(trifluoromethyl)phenyl)-4,5-dihydro-1H-1,2,4-triazol-3-yl)propyl)-[1,1'-biphenyl]-3-yl)acetic acid, 2-(4-ethoxy-4'-(3-(5-oxo-4-(o-tolyl)-1-(4-(trifluoromethyl)phenyl)-4,5-dihydro-1H-1,2,4-triazol-3-yl)propyl)-[1,1'-biphenyl]-3-yl)acetic acid, and 2-(4-ethoxy-4'-(3-(5-oxo-4-(pyridin-3-yl)-1-(4-(trifluoromethyl)phenyl)-4,5-dihydro-1H-1,2,4-triazol-3-yl)propyl)-[1,1'-biphenyl]-3-yl)acetic acid, or a pharmaceutically acceptable salt thereof.

18. A pharmaceutical composition comprising a compound of claim 1, or a pharmaceutically acceptable salt thereof, and at least one pharmaceutically acceptable carrier.

19. A method of treating cancer in a mammal which is negatively impacted by diminution in its metabolism of fatty acid oxidation, comprising administration of a therapeutically effective amount of a compound of claim 1, or a pharmaceutically acceptable salt thereof, to the mammal in need thereof.

20. The method according to claim 19, wherein the cancer is selected from prostate, breast, ovarian, liver, kidney, colon, pancreatic, human chronic lymphocytic leukemia, and melanoma.

21. A method of treating cancer in a mammal comprising the administration of a therapeutically effective amount of a compound of claim 1, or a pharmaceutically acceptable salt thereof, to the mammal in need thereof.

22. The method according to claim 21, wherein the cancer is prostate, breast, ovarian, liver, kidney, colon, pancreatic, human chronic lymphocytic leukemia, or melanoma.

23. A compound of claim 1 selected from the group consisting of:

2-(4'-(3-(4-cyclohexyl-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4-ethoxy-4'-(3-(5-oxo-4-phenyl-1-(4-(trifluoromethyl)phenyl)-4,5-dihydro-1H-1,2,4-triazol-3-yl)propyl)-[1,1-biphenyl]-3-yl)acetic acid, 2-(4'-(3-(4-(2-chlorophenyl)-5-oxo-1-(4-(trifluoromethyl)phenyl)-4,5-dihydro-1H-1,2,4-triazol-3-yl)propyl)-4-ethoxy-[1,1'-biphenyl]-3-yl)acetic acid, 2-(4-ethoxy-4'-(3-(4-(3-fluorophenyl)-5-oxo-1-(4-(trifluoromethyl)phenyl)-4,5-dihydro-1H-1,2,4-triazol-3-yl)propyl)-[1,1-biphenyl]-3-yl)acetic acid, 2-(4'-(3-(4-(2,5-difluorophenyl)-5-oxo-1-(4-(trifluoromethyl)phenyl)-4,5-dihydro-1H-1,2,4-triazol-3-yl)propyl)-4-ethoxy-[1,1-biphenyl]-3-yl)acetic acid, 2-(4-ethoxy-4'-(3-(4-(2-fluorophenyl)-5-oxo-1-(4-(trifluoromethyl)phenyl)-4,5-dihydro-1H-1,2,4-triazol-3-yl)propyl)-[1,1-biphenyl]-3-yl)acetic acid, and 2-(4-ethoxy-4'-(3-(1-(4-(trifluoromethyl)phenyl)-5-oxo-4-(4-(trifluoromethyl)phenyl)-4,5-dihydro-1H-1,2,4-triazol-3-yl)propyl)-[1,1'-biphenyl]-3-yl)acetic acid, or a pharmaceutically acceptable salt thereof.

* * * * *